(12) United States Patent
Fuchs

(10) Patent No.: US 7,390,620 B2
(45) Date of Patent: Jun. 24, 2008

(54) SCREENING METHOD FOR ANTI-MICROBIAL DRUG TARGETS BY GENOME-SATURATING MUTAGENESIS (GSM)

(75) Inventor: Thilo M. Fuchs, Augsburg (DE)

(73) Assignee: Creatogen Laboratories GmbH, Potsdam (DE)

( * ) Notice: Subject to any disclaimer, the term of this patent is extended or adjusted under 35 U.S.C. 154(b) by 576 days.

(21) Appl. No.: 10/474,214

(22) PCT Filed: Apr. 8, 2002

(86) PCT No.: PCT/EP02/03874

§ 371 (c)(1),
(2), (4) Date: Oct. 6, 2003

(87) PCT Pub. No.: WO02/083940

PCT Pub. Date: Oct. 24, 2002

(65) Prior Publication Data

US 2004/0132041 A1 Jul. 8, 2004

(30) Foreign Application Priority Data

| Apr. 6, 2001 | (EP) | 01108774 |
| Apr. 27, 2001 | (EP) | 01110443 |
| Aug. 22, 2001 | (EP) | 01120181 |

(51) Int. Cl.
 C12Q 1/02 (2006.01)
 C12Q 1/68 (2006.01)
(52) U.S. Cl. ............................ 435/6; 435/29
(58) Field of Classification Search ............ 435/6, 435/29
 See application file for complete search history.

(56) References Cited

U.S. PATENT DOCUMENTS

| 5,756,347 A * | 5/1998 | Sugimoto et al. ......... 435/320.1 |
| 6,348,328 B1 * | 2/2002 | Black et al. ................ 435/69.1 |

FOREIGN PATENT DOCUMENTS

| WO | WO 98/50402 A1 | 11/1998 |
| WO | WO 99/04637 A1 | 2/1999 |
| WO | WO 99/15644 A2 | 4/1999 |
| WO | WO 99/28508 A1 | 6/1999 |
| WO | WO 00/73502 A2 | 12/2000 |
| WO | WO 01/77295 A1 | 10/2001 |
| WO | WO 02/00916 A2 | 1/2002 |
| WO | WO 02/092814 A2 | 11/2002 |

OTHER PUBLICATIONS

Lee et al. Applied and Environmental Microbiology, May 1999, p. 1883-1890.*
Arigoni et al. Nature Biotechnology vol. 16 p. 851-856 1998.*
Tohe et al. Genes Genet. Syst. vol. 75 p. 33-39 , 2000.*
Arigoni, Fabrizio, et al., "A genome-based approach for identification of essential bacterial genes", Nature Biotechnology, Sep. 1998, vol. 16, pp. 851-856.
Chalker, Alison F. et al., "Systematic Identification of Selective Essential Genes in *Helicobacter pylori* by Genome Prioritization and Allelic Replacement Mutagenesis", Journal of Bacteriology, Feb. 2001, vol. 183, No. 4, pp. 1259-1268.
Joyce, Catherine M. et al., "Method for Determining Whether a Gene of *Escherichia coli* Is Essential: Application to the poIA Gene", Journal of Bacteriology, May 1984, vol. 158, No. 2, pp. 636-643.
Judson, Nicholas, "Transposon-based approaches to identify essential bacterial genes", Trends in Microbiology, Nov. 2000, vol. 8, No. 11, pp. 521-526.
Lee, Myeong S., et al., "Insertion-Duplication Mutagenesis in *Streptococcus pneumoniae*: Targeting Fragment Length is a Critical Parameter in Use as a Random Insertion Tool", Applied and Environmental Microbiology, Dec. 1998, vol. 64, No. 12, pp. 4796-4802.
Lee, Myeong S., Construction and Analysis of a Library for Random Insertional Mutagenesis in *Streptococcus pneumoniae*: Use for Recovery of Mutants Defective in Genetic Transformation and for Identification of Essential Genes, Applied and Environmental Microbiology, May 1999, vol. 65, No. 5, pp. 1883-1890.
Morrison, Donald A. et al., "Isolation of Transformation-Deficient Streptococcus pneumoniae Mutants Defective in Control of Competence, Using Insertion-Duplication Mutagenesis with the Erythromycin Resistance Determinant of pAMβ1", Journal of Bacteriology, Sep. 1984, vol. 159, No. 3, pp. 870-876.
Reich, Karl A., "Genome Scanning in *Haemophilus influenzae* for Identification of Essential Genes", Journal of Bacteriology, Aug. 1999, vol. 181, No. 16, pp. 4961-4968.
Reich, Karl A., "The search for essential genes", Research Microbiology, Feb. 25, 2000, vol. 151, pp. 319-324.
Schmid, Molly B., "Novel approaches to the discovery of antimicrobial agents", Current Opinion in Chemical Biology, 1998, vol. 2, pp. 529-534.

* cited by examiner

*Primary Examiner*—Mark Navarro
(74) *Attorney, Agent, or Firm*—Rothwell, Figg, Ernst & Manbeck, P.C.

(57) ABSTRACT

This invention relates to a novel method for the identification of obligatory essential nucleic acid sequences, in particular microbial sequences. Further, a method for the identification of novel antimicrobial compounds using the obligatory essential nucleic acids and proteins encoded thereby is provided.

12 Claims, 5 Drawing Sheets

Figure 1: Steps a-e of the screening method for the identification of obligatory essential genes

Step a: fragment library from *Salmonella enterica* serovar Typhimurium in ts-vector is transformed in host strain EC101, growth at 30°C

↓

Step b: preparation of plasmid-DNA and transformation in *Salmonella enterica* serovar Typhimurium, growth at 30°C

↓

Step c: insertional duplication mutagenesis by homologous recombination

 =clone without insert or fragment from obligatory essential gene

●○○●○○○○○○○○
○○●○○○○○○○○○
○○○○○○●○●●○○
○○○○○○○○○○●○
○●○○○○○●○○○○
○○●○○○○○○○○○
○○○○●●○○○●○○
○○○○●○○○○○○●

↓

Step d: growth of all integrants at 38.5°C temperature; clones with insertless vector or essential fragment do not grow ○○ ○○○○○○○○
○○ ○○○○○○○○
○○○○○○ ○  ○○
○○○○○○○○○ ○
○ ○○○○○ ○○○○
○○ ○○○○○○○○
○○○○   ○○○ ○○
○○○○ ○○○○○○

↓

Step e: PCR and sequencing of all clones with insert

Figure 2: Genome-saturating mutagenesis. The operon structure of a genomic fragment of 15900 bp is shown. Insertions within the ORF 5-7 and the essentiell gene are detected by GSM. Due to transcriptional coupling, insertions upstream of the essential gene are lethal. However, since an insertion within the last ORF does not result in a viable phenotype, this ORF and not the others is essential.

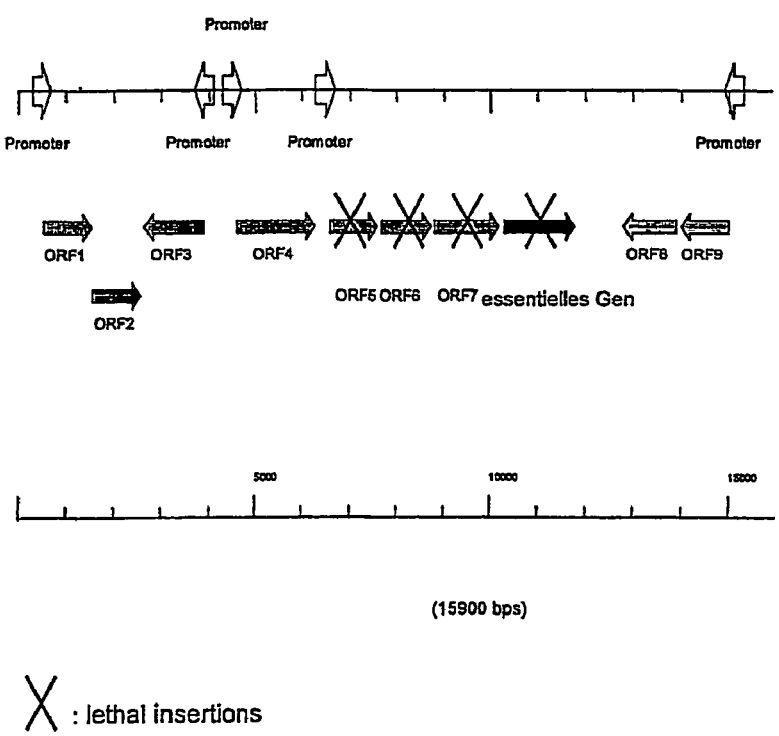

Figure 3: Plasmids for insertional duplication mutagenesis.
pIDM shows a plasmid harbouring the origin of replication, a selectable marker, a multiple cloning site and a replication protein. A conditionally replicating vector must not provide a essential replication protein which might be chromosomally encoded (see description).
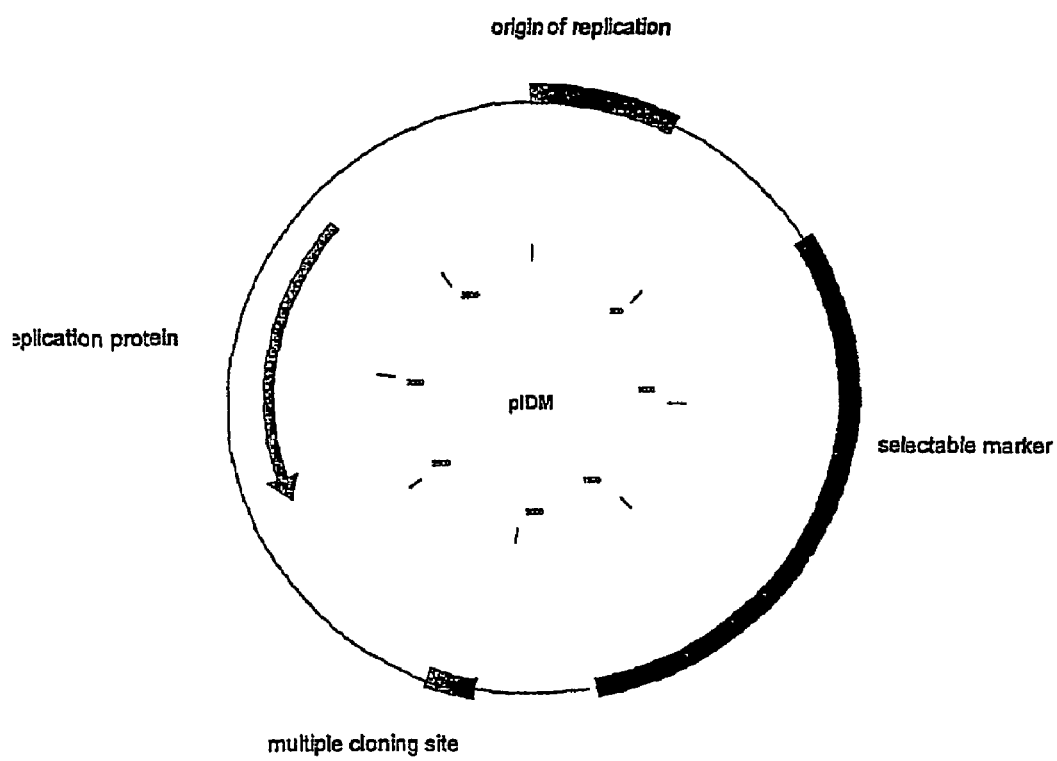

Fig. 4: Insertional mutagenesis by homologous recombination. An intragenic fragment of ~400 bp is cloned into the vector pIDM. A cointegrate structure is formed by homologous recombination resulting in fragment duplication and interruption of the targeted ORF. Integrants can be selected by appropriate growth conditions, and their phenotype can be characterized.

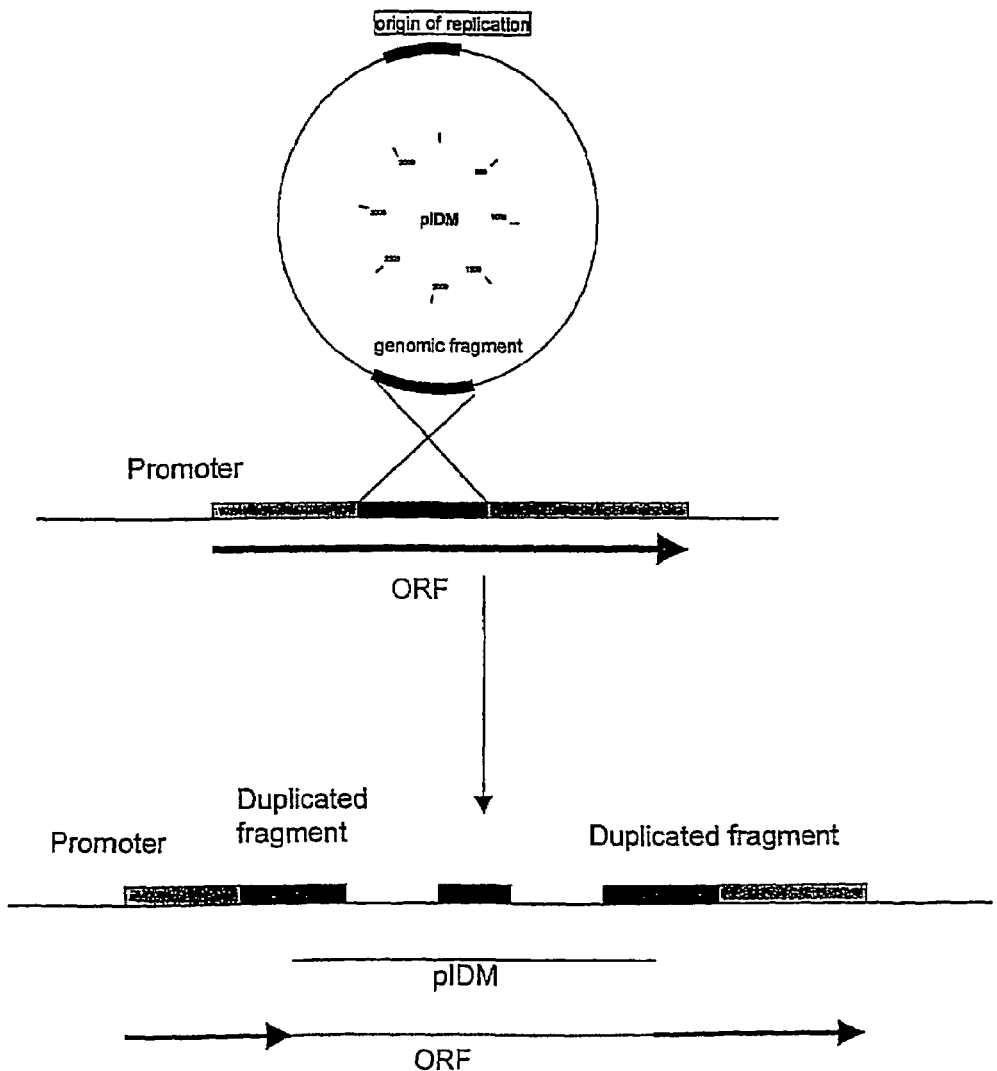

Fig. 5: pIDM001 is the vector used for mutagenesis of
S. typhimurium as described in the example. It harbours
a temperature-sensitive replication protein, an origin of replication,
a tetracycline-resistance gene and a multiple cloning site.
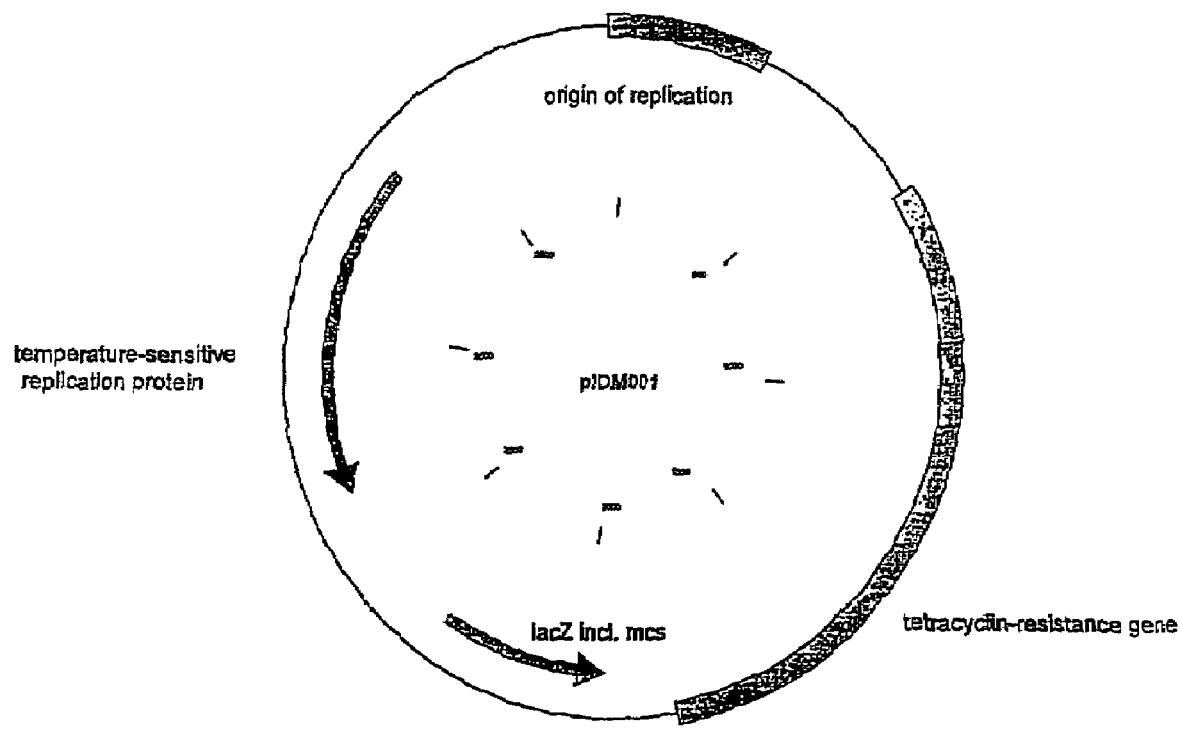

SCREENING METHOD FOR ANTI-MICROBIAL DRUG TARGETS BY GENOME-SATURATING MUTAGENESIS (GSM)

CROSS REFERENCE TO RELATED APPLICATION

This is application is a 35 USC §371 National Phase Entry Application from PCT/EP02/03874, filed Apr. 8, 2002, and designating the U.S.

This invention relates to a novel method for the identification of obligatory essential nucleic acid sequences, in particular microbial sequences. Further, a method for the identification of novel antimicrobial compounds using the obligatory essential nucleic acids and proteins encoded thereby is provided.

One of the main achievements of medicine in the past century was the use of antimicrobial drugs to control infectious diseases. However, despite the enormous advances in health care, infectious diseases still account for 25% of deaths worldwide and 45% in low-income countries (World Health Orcianization-World Health Report). Prior to the 1980s, bacterial infections in developed countries could be readily treated with available antibiotics. During the 1980s and 1990s however, antibiotic resistant bacterial strains emerged and have become a major therapeutic problem. There are, in fact, strains resistant to essentially all of the commonly used antibacterial agents, which have been observed in the clinical setting. In the United States alone, some 14,000 people are infected and die each year as a result of drug-resistant microbes picked up in hospitals. Around the world, as many as 60% of hospital-acquired infections are caused by drug-resistant microbes. The consequences of the increase in resistant strains include higher morbidity and mortality, longer patient hospitalization, and an increase in treatment costs. In this context a common misconception is that the pharmaceutical industry is frequently making new drug discoveries to replace those drugs that become ineffective in fighting the major infectious diseases. In reality, while new versions of older drugs continue to be developed, there is a dearth of new classes of antibacterials not significantly affected by the existing bacterial resistance mechanisms.

In the early years of penicillin use pathogens dependend on a single resistance mechanism evolved, whereas many strains found in the clinic today have acquired multiple systems to reduce or avoid the action of an antibiotic. Most threatening of these are mechanisms that involve changes in the target site for antibiotic interaction, conferring levels of resistance to all compounds with that same mechanism of action. Furthermore, the DNA coding for these processes can be transferred between related strains, and the short generation time of many microorganisms facilitates the opportunity for gene selection even during a short course of drug treatment.

There is therefore a need for a range of new drugs with new mechanims of action, not susceptible to existing resistance mechanisms and in sufficient numbers to reduce reliance on a small number of chemical classes.

The development of new antibacterial agents can proceed by a variety of methods, but generally fall into at least two categories. The first is the traditional approach of sceening for antibacterial agents without concern for the specific target. The second approach involves the identification of new targets, and the subsequent screening of compounds to find antibacterial agents affecting those targets. Such screening can involve ad any of a variety of methods, including screening for inhibitors of the expression of a gene, or of the product of a gene, or of a pathway requiring that product. However, generally the actual target is a protein, the inhibition of which prevents the growth or pathogenesis of the bacterium. Targets for antiinfectiva can be found by identifying genes encoding proteins essential for bacterial growth.

Several approaches have been described so far to identify putative essential nucleic acid sequences. These include:

1. Signature Tagged Mutagenesis (STM), or Subtractive Recombination Mutagenesis (SRM)

Both methods are based on insertional mutagenesis, either by transposons or by homologous recombination. Clones with an insertion genotype are generated in vitro and selected by cell culture or a mouse model to identify genes essential for cell growth under in vivo conditions (Patent Application WO 00/73502; Hensel, 1995; Holden, 1998). However, mutants with insertions in genes or operons which are obligatory essential for cells in terms of viability on rich medium cannot be identified by these methods.

2. Conditional Mutations Affecting Growth

This effort to identify genes essential for the growth of Gram-positive bacteria bases on a collection of temperature sensitive mutants generated by chemical or UV mutagenesis (Martin, 1999). It is supposed that gene products which can mutate to conditional lethality are generally considered essential for viability (Schmid, 1998). Mutated colonies are replica plated in duplicate and incubated either under permissive or not permissive growth conditions. Temperature-sensitive mutants are complemented by transformation of a wild-type library into a helper strain followed by phage infection and transduction. Complementing clones of 2-8 kb are characterized further.

One of the disadvantages of temperature-sensitive mutant strategies is the differential ability of some proteins to achieve thermolabile mutant forms (Harris, 1992; Schmid, 1989). Approximately one third of proteins cannot mutate to a thermolabile form, which makes it difficult to isolate conditional mutants in certain genes. Furthermore, complementation of the selected mutants, sequencing of the complementing genome regions and validation of targets are time intensive. Many targets identified by this approach will already be known proteins like replicases, enzymes involved in cell wall synthesis or protein biosynthesis. Other drawbacks of this approach are that the mapping is not possible without great effort and that random screens for temperature sensitive (TS) mutants can result in jackpots created by repeated isolation of the same mutant classes, presumably because such gene products are particularly easy to mutate to TS alleles. In addition, a few genes have been identified so far that are required for viability at high temperatures, which will lead to false assignment of a few genes as essential under all growth conditions (Schmid, 1998).

3. Targeted Knockout Approaches

Targeted knockout approaches like the *Saccharomyces cerevisiae* or *Bacillus subtilis* functional analysis program (Winzeler, 1999) were performed by systematical investigation of every gene in one organism (Loferer, 2000). By genome prioritization, single loci of interest are knocked out or conditionally expressed, and features like cell growth variation or essentiality under different conditions are determined. Targeted knockout approaches are very resource intensive and cannot be applied to a broad range of pathogenic microbes.

4. Comparative Genomics (Chalker, 2001; Arigoni, 1998; Hutchison, 1999).

Comparative genetic analysis of closely related genomes helps to detect differences between pathogenic and non-pathogenic variants. Furthermore, genes of yet unknown functions which are conserved in the compact genome of *Mycoplasma genitalium* have been tested for essentiality in other bacteria using a knockout strategy. A recent approach (WO 00/61793) identified 26 *E. coli* ORF that are both of unknown function and conserved in the compact genome of *Mycoplasma genitalium*. Six of the 26 ORF have been shown to be essential in *E. coli* (Arigoni, 1998). On the other hand, several genes which are conserved in *H. pylori* but highly diverged in other eubacteria were screened using a vector-free allelic replacement mutagenesis technique (Chalker, 2001).

By genome comparison between the two smallest bacterial genomes sequenced so far, Mushegian and Koonin postulated that 256 genes are close to the minimal set that is necessary and sufficient to sustain the existence of a bacterial cell (Mushegian, 1996). However, as shown by (Arigoni, 1998) only 6 of 26 orthologous gene loci in *E. coli* out of the Mycoplasma set revealed to be essential for viability. An automated BLASTP-based genome comparison to identify *E. coil* FUN genes resulted in a list of 65 candidate genes which are conserved between several pathogens (WO 00/61793). Among them, 36% gave no deletion genotype.

Thus, comparative genomics will not cover the whole set of essential nucleic acid sequences of different pathogens. Moreover, only few organism specific genes will be identified by this approach.

5. Genomic Footprinting and Transposon Mutagenesis (Wong, 2000; Rubin, 1999; Judson, 2000a; Judson, 2000b; Lehoux, 1999; Takiff, 1992; Akerley, 1998; Reich, 1999; Hare, 2001).

Transposons provide a further method for defining essential nucleic acid sequences (overview: Judson, 2000b). Conceptually, there are two ways to identify essential genes or regions of the bacterial chromosome: i) the negative approach, which identifies many regions that are not essential and presumes that everything else is essential (Hutchison III, 1999), and ii) the positive approach Which identifies genes that are essential by generating a conditional mutation and showing that is has a lethal phenotype (Judson, 2000b).

i) The negative approach can define sites within an otherwise essential ORF that are permissive for insertions. However, it does not identify essential nucleic acid sequences. Further strain construction is required to confirm essentiality of putative essential nucleic acid sequences. Problems posed by operon structures cannot be solved without detailed analysis. PCR-mapping approaches define non-essential regions by in vitro transposition and PCR on a short, defined segment of DNA. Large-scale analysis is resource intensive, expensive and restricted to naturally competent organisms. Global transposon mutagenesis is performed to analyze a large number of a random chromosomal insertions to define regions that cannot be hit. This method is very resource intensive and can only be applied to a limited number of chromosomal loci. Saturation of a genome is not obtainable.

ii) Positive approaches identify essential nucleic acid sequences by substitution of an essential gene's natural promoter with an inducible one, generating a conditional mutation. For example, the TnAraOut system (Judson, 2000a) uses the arabinose promoter with a large induction ratio. The transposon has a broad host range transposon with a small target sequence. Tn-mutants are replica-plated and incubated either with or without arabinose induction. Colonies which do not grow without arabinose might have substituted the promoter of an essential gene by the arabinose-induced promoter. Chromosomal DNA of this mutant is isolated, and the targeted region is cloned or amplified via inverse PCR.

However, insertions upstream of every essential gene might not be possible. Saturating mutagenesis of a genome is laborious to achieve. One of the reasons lies in the fact that expression levels of the inducible promoter will not be broad enough to identify every essential gene. This means that an inducible promoter might not provide expression levels which are high enough to overcome the defect created by knocking out the natural promoter. Conversely, basal expression of an inducible promoter might be too high with severe consequences for bacterial growth including bacteriostasis. These genes will not be identified by said method (Judson, 2000b).

Operon structures pose several problems which are not solved by the positive approaches. For example, polar effects from the presence of an insertion can be severe, limiting insertions upstream of an essential gene. In addition, if translation of a downstream essential gene is coupled to a gene that is disrupted by the presence of the insertion, these insertions will not be found.

In addition, the size of the target in which an insertion can occur varies will generally be small and depends on the gene. Therefore, it might be difficult or impossible to inhibit certain genes.

Taken together, no satisfying method to identify obligatory essential nucleic acid sequences of microorganisms which is further quick, easy and upscalable is known from state of the art.

Thus, the underlying problems leading to the present invention was to provide an improved method for the identification of obligatory essential nucleic acid sequences and means for the development of novel antimicrobial drugs that can be used for a broad spectrum of infections or disorders related to microbial infections.

The solution to the above problem is achieved according to the invention by providing the embodiments characterized in the claims.

Accordingly, the present invention relates to a method for the identification of obligatory essential microbial nucleic acid sequences comprising the steps (a) providing a conditionally replicating vector, comprising
  (i) a conditionally replicating origin of replication
  (ii) a selectable marker
  (iii) a nucleic acid sequence of a microorganism
(b) transforming microbial host cells with said conditionally replicating vector, wherein the host cell is selected such that the nucleic acid sequence of (a) (iii) is sufficiently homologous to an endogenous a nucleic acid sequence of the host cell in order to allow homologous recombination
(c) subjecting the transformed host cells to insertional duplication mutagenesis by homologous recombination, resulting in viable and non viable integrants
(d) identifying lethal integrants
(e) characterizing nucleic acid sequences from lethal integrants and/or polypeptides encoded thereby which are obligatory essential for the viability of said microorganism.

In the graph of FIG. 1 an example to perform the method of the invention is depicted without implying any limitations.

The method as described has several advantages over methods state of the art identifying obligatory essential microbial genes. Some advantages as listed in Table 1 are:

Obligatory essential nucleic acid sequences and polypeptides encoded thereby can be exclusively identified.

The approach can be genome saturating, e.g., all loci that are obligatory for cell viability, can be identified, including those which are yet unknown comprising a large set of nucleic acid sequences and/or polypeptides.

The method as presented is faster than comparable approaches, cost effective and easily upscalable.

The method can be applied to any microorganism with an effective recombination system and for which means of transformation is available.

Application of the method of the invention to a pathogenic strain results directly in identification of all obligatory essential nucleic acid sequences providing new targets for novel broad-and narrow-range drugs.

TABLE 1

Features of different methods identifying obligatory essential nucleic acid sequences

| | Present invention | Conditional lethal mutations | Transposon-Mutagenesis, GAMBIT | Comparative genomics |
|---|---|---|---|---|
| Genome representation | genome saturating | not saturating (<66%) | not saturating | not saturating |
| Range of application | all transformable bacteria | all | not applicable to all bacteria | all |
| Identification of targeted gene | directly, fast | indirectly, resource intensive | indirectly, resource intensive | limited to complete genome sequences |
| Comparative genomics | possible | limited | limited | possible |
| Knockout of unknown ORFs | all | <66% | not saturating | few |

If a genome-representing nucleic acid sequence library of a microorganism of interest (also called fragment library) is established in a conditionally replicating vector, the method may comprise a substantially genome saturating mutagenesis. Genome saturating mutagensis according to the invention means that each single clone of a genome-representing library is subjected to the claimed method. "Substantially" means that at least 90%, preferably at least 95% and more preferably at least 99% of the clones are tested. The test may be carried out in a high-throughput system, e. g., in a microtiter plate. An insertion frequency of at least three insertions per kilobase of target DNA, particularly of four to six insertions per kilobase is preferred.

An important feature of genome saturating mutagenesis according to the invention is that those genomic fragments which are identified and further investigated contain an obligatory essential nucleic acid sequence. This is not only an advantage in comparison to a "negative" approach like transposon-mutagenesis that identifies only gene loci which can be disrupted by insertional mutagenesis without loss of cell viabilitiy. Moreover, since every ORF in an operon will be mutagenized, polar effects can be studied rapidly, instead of analyzing an operon by time-consuming subsequent knock out steps. For example, if within an operon of 4 ORF (s. FIG. 2) four different intragenic lethal insertions are detected, presumably the ORF at the 3'-end of the operon is the obligatory essential nucleic acid. Thus, a preferred embodiment relates to a method according to the invention, wherein step (c) comprises a substantially genome saturating mutagenesis.

As stated above, the invention can be applied to any microorganism of interest. A particularly preferred embodiment therefore relates to a method, wherein said nucleic acid sequence of step (a) is derived from a microorganism selected from bacteria and yeasts, particularly from Gram-positive and Gram-negative bacteria. Organisms of interest thereby can be selected from pathogenic microorganisms such as *Escherichia coli, Bacillus subtilis, Haemophilus influenzae, Helicobacter pylori, Borrellia burgdorferi, Treponema pallidum, Streptococcus pneumoniae, Enterococcus faecalis, Pseudomonas aeruginosa, Bordetella pertussis, Chlamydium trachomatis* and others.

The method as claimed herein comprises several steps, which are described in more detail below:

Step (a) Comprises Providing a Conditionally Replicating Vector

A conditionally replicating vector useful in the present invention comprises a conditionally replicating origin of replication.

In general, vectors comprise defined regions called "origin of replication" that are activated by the binding of replication proteins. A conditionally replicating vector replicates only under certain conditions, e. g. in the presence of a specific replication protein. Thus, such a conditionally replicating vector does not replicate in a host strain without replication protein or due to a lack of expression of the protein. Furthermore, a protein which is necessary for the replication of the vector, might be active only under certain conditions, e. g. at a certain temperature (which is called permissive temperature). At another temperature (which is called non-permissive), the replication protein might be inactive.

Conditional inactivation of a replication protein can occur by mutagenesis of its gene sequence. A mutation can result in changing the amino acid sequence of the replication protein providing a protein which still might be active under permissive temperature. However, under non-permissive conditions, temperature, the protein is inactive due to its mutations. Inactive means that the protein does not bind to the origin of replication in the same manner as the wild-type protein. Temperature shifts from permissive to non-permissive temperature results in conformational changes in the mutated replication protein, followed by protein inactivation and lack of vector, replication. Therefore, such a protein is called temperature-sensitive (Maguin, 1992).

A replication protein: necessary for vector replication can be encoded by the vector itself, by an additional vector or chromosomally and, if desired, under control of a regulatory expression control sequence.

In addition, a conditionally replicating vector as used herein comprises a selectable marker. A selectable marker is any genetic region carried by a plasmid that alters the ability of a cell harboring the plasmid to grow or survive in a given growth environment relative to a similar cell lacking the selectable marker. Thus, a selection of bacterial cells harboring said vector in favor to cells which do not harbor said vector can be performed. Preferably, a selectable marker provides resistance to an antibacterial compound (antibiotic resistance marker). However, other selectable markers are known from state of the art. Auxotrophy markers e. g., allow growth of an otherwise not viable cell by complementing a genetic defect of said cell.

A bacterial strain harboring a conditionally replicating vector can be cultivated under permissive conditions, e. g., permissive temperature, and under selectable conditions. A shift to non-permissive temperature results in lack of replication of the conditionally replicating vector. That means that during bacterial growth at non permissive temperature, copies of the vector are subsequently segregated, and due to loss of the vector the bacteria cannot grow further.

Examples for conditionally replicating vectors are temperature-sensitive plasmids like pVE6007 or pKO3 (Link, 1997; Biswas, 1993). The origin-specific replication protein usually defines the factor which is responsible for temperature sensitivity because of mutations of its amino sequence. The replication protein is encoded either on the plasmid itself or on the chromosome (temperature-sensitive vector). Non-permissive temperature renders the replication protein inactive due to changes in its conformation. An example for an improved conditionally replicating vector is pIDM (FIG. 3) that can be applied to Gram-negative and to Gram-positive microorganisms. An important feature of the pIDM-vector is that in addition to the origin of replication and the selectable marker, it harbors the temperature-sensitive replication protein which therefore must not be provided in trans.

Furthermore, the conditionally replicating vector as used herein contains genomic nucleic acid sequences (fragments) of a microorganism. These nucleic acid sequences are preferably of a defined length of about 200 to 2000 bp, more preferably of about 300 to 600 bp and can be generated by cleaving chromosomal DNA by appropriate restriction enzymes or by random PCR amplification (Froussard, 1992). The nucleic acid sequences are inserted into the vector by ligation with a linearized vector molecule. This ligation occurs at a specific site within a conditionally replicating vector called cloning site. A cloning site may be a multiple cloning site and may allow the selection for vector molecules with inserted nucleic acid sequence (insert) against those without insert. An example for such a selection system is called blue/white selection by alpha-complementation of the LacZ protein as described by (Sambrook, 1989).

If the cloned fragments are of an appropriate high number and represent the complete genome of an microorganism, each chromosomal nucleic acid sequence is cloned at least once. Thus, the pool of recombinant vector molecules are called a genome-representing nucleic acid sequence or fragment library.

Step (b) comprises transforming microbial host cells with said conditionally replicating vector. A vector molecule or a vector with inserted fragment or a fragment library as defined under (a) can be transformed into microbial host cells by any suitable method for example by electroporation, protoplasts, liposomes, calcium phosphate, DEAE dextran, calcium chloride etc. Preferably, the vector pIDM (FIG. 3) as described herein or a derivative thereof is used.

Host cells can be transformed in pools or, preferably, as single cells. Transformants are cultivated under permissive conditions. Selection of transformed bacteria can be performed via the selectable marker. A transformant as used herein means a bacterial host cell that harbors the conditionally replication vector with or without genomic insert. Growth of transformed cells under selective pressure takes place preferably under permissive conditions.

Step (c) Comprises Subjecting the Transformed Host Cells to Insertional Duplication Mutagenesis by Homologous Recombination A conditionally replicating vector containing a genomic nucleic acid sequence of a microorganism can be used for insertional duplication mutagenesis (IDM) (Patent Application WO 00/73502; Maguin, 1992; Hashimoto-Gotoh, 1981; Kok, 1984; Metcalf, 1994, Metcalf, 1996; Link, 1997).

The term "IDM" as used herein means that an extrachromosomal nucleic acid sequence can recombine with an identical chromosomal nucleic acid sequence in the presence of an effective recombination system provided by the host cell thereby resulting in an insertional duplication as described below. This event called "homologous recombination" occurs statistically at a rate of 3.0E-02 to 5.0E-5 (Biswas, 1993) and depends on the length of the sequence and/or the chromosomal site of integration.

If said genomic fragment is cloned in a vector like a conditionally replicating vector, homologous recombination and therefore "IDM" can occur at permissive conditions and results in insertion of the vector into the chromosome (FIG. 4). Under permissive conditions the vector is able to a replicate. Thus, in a preferred embodiment of the present invention insertional mutagenesis of step (c) takes place under permissive conditions, allowing the provided vector in step (a).

During recombination, a so-called "cointegrate" between both nucleic acid sequences (vector and chromosome) is formed, resulting in chromosomal insertion (resulting in an insertional genotype) and duplication of said sequence (FIG. 4). The term "insertional genotype" as used herein means a cell whose chromosome is characterized by a cointegrate formation between a cloned nucleic acid sequence and its homologue on the chromosome.

The integration rate per cell depends on the length of the cloned genomic nucleic acid, the copy number of the vector and/or the, chromosomal structure. The term "chromosome" as used herein includes the whole genome of a microbial cell. Plasmids encoding any cell function are part of the chromosome per definition.

Under permissive conditions, an equilibrium between extrachromosomally (in trans) replicating and chromosomally inserted vector is established. The term "extrachromosomally" as used herein means that the vector replicates within the cytosol.

On the other hand, under non-permissive conditions, the equilibrium is completely shifted to chromosomally inserted vectors and thereby to insertional genotypes. Cells in which the vector is inserted via homologous recombination, are called "integrants". If the respective fragment is part of an open reading frame (ORF), this ORF is disrupted by the insertion and thus mutagenized. If a genome-representing fragment library is derived from a microbial organism and transformed into the same organism as a host, homologous recombination and mutagenesis can be directed to any site of the chromosome. Insertional genotypes or integrants are only viable if integration has taken place in a non essential nucleic acid sequence. To the contrary, insertional mutagenesis of an obligatory essential nucleic acid sequence is not viable per definition. Selection for integrants occurs via the plasmid-encoded selectable marker.

Step (d) Comprises Identifying Lethal Integrants

Colonies obtained by transformation of a genome-representing fragment library into a microorganism can be isolated in rich medium or other growth medium. This results in a genome-representing library of isolated transformants, each of them harboring a clonal copy of a conditionally replicating vector like the pIDM-vector with a specific genomic nucleic acid sequence. During growth of these transformants, clonal division takes place. "Clonal division" as used herein means that two types of cells exist within one single clone: cells with the conditionally replicating vector in trans (e. g., extrachromosomally) or cells with chromosomally inserted vector via homologous recombination.

These two types of cells can be separated in a step called "replica plating". The term "replica plating" as used herein means that a defined number of clonal or clonal divisioned microbial cells (e. g., a single colony or a defined dilution of this single colony obtained in step (b)) is grown under permissive and under non permissive conditions. Under selective pressure and non permissive conditions only cells with a chromosomally inserted vector will grow, whereas the other type of cells with a extrachromosomal vector will not grow due to segregation of the conditionally replicating vector and consequent loss of resistance against the selection marker. Accordingly, a preferred embodiment of the invention relates to a method, wherein identifying lethal integrants of step (d) is performed by replica plating. The lethal integrants may be identified by other suitable methods.

By separating the two types of cells by replica plating as described herein, a screening for clones, preferably single clones, can be performed which are characterized by a lack of viable integrants. The latter represent cells with an insertion into an obligatory nucleic acid sequence since integration of a vector containing an intragenic fragment of an obligatory essential sequence is lethal for the respective cell.

The term "obligatory essential nucleic acid sequence" as used herein means that an intact copy of such a sequence is necessary for bacterial growth. Thus, clones without viable insertional genotype can be identified by replica plating (FIG. 1).

Using a genome-representing fragment library, the method is genome-saturating and all clones with a fragment being part of an obligatory nucleic acid sequence can be identified by replica plating as described herein.

In accordance with the above, a preferred embodiment of the invention relates to a method, wherein replica plating is performed using permissive and non-permissive conditions and lethal integrants are identified by separating viable and non viable integrants of step (c) under permissive conditions versus non-permissive conditions.

Clones without viable insertional genotype under non permissive conditions screened by replica plating as described under (d) can be characterized further by any suitable method, e. g., amplification of nucleic acids, preferably via polymerase chain reaction (PCR). Accordingly, in a preferred embodiment of the invention, characterizing the lethal integrants in step (e) comprises nucleic acid amplification, particularly PCR.

The fragments obtained by nucleic acid amplification can be sequenced starting at the cloning site. Using data base searches, the obtained sequence can be compared to sequence information, e.g., the complete genome sequence available for the mutagenized organism or a related organism. The chromosomal site which has been targeted by insertional mutagenesis can thereupon be mapped to analyze its chromosomal structure in terms of operon structure, promoter consensus sequences and other features important for the identification of the obligatory essential gene or sequence. An obligatory essential nucleic acid sequence can thereby either be identified as an obligatory essential gene or as a regulatory sequence like an enhancer or a promoter. The nucleic acid sequence of a gene can be translated, and the obtained amino acid sequence can be compared to proteins in known databases. In case that no sequence information is available of the nucleic acid sequences of the microorganism which has been investigated, the flanking regions have to be sequenced.

Step (e) comprises characterizing nucleic acid sequences from lethal integrants and/or polypeptides encoded thereby which are obligatory essential for the viability of said microorganism.

The obligatory essential nucleic acid sequence identified by the method can have different functions in terms of viability of the microorganism. However, the targeted sequence is not necessarily an essential gene or sequence itself but can cause cell death due to polar effects.

The term "polar effects" as used herein means that a lethal phenotype is not due to the mutagenesis of the sequence itself for which a lethal insertional mutagenesis was obtained. For example, if the genes of an operon are transcriptionally or translationally coupled, insertional mutagenesis of others than the obligatory essential gene might be lethal.

Characterization of a nucleic acid sequence and/or polypeptide encoded thereby which is essential for cell viability can be performed in several steps:

If the identified fragment is part of an operon according to the annotation data, polar effects might be responsible for the lethal genotype of the IDM of the respective fragment. Therefore, sequences within the same operon can be devised to IDM. For example, intragenic fragments of genes which were not identified via the described method can be cloned into a conditionally replicating vector, and subsequent IDM of all sequences of an operon can be performed.

Non polar gene deletions of the respective locus can be introduced to identify the obligatory essential nucleic acid sequence; thus, any polar effects can be excluded. Examples for this strategy are described by (Brown, 1995; Chalker, 2001). Gene deletions are in trans complemented with the wild-type allele under the control of an inducible promoter.

From the results of the method, a chromosomal map can be established. This map shows all sequences which are are linked with viability of the investigated microorganism. Thus, if an insertion has taken place within an operon, other lethal recombination events within the respective operon or gene complex have to be investigated.

The identification and characterization of nucleic acid sequences and/or polypeptides encoded thereby which are essential for the viability of microorganisms can be performed via comparative genomics. Thus, a preferred embodiment relates to a method, wherein characterization of nucleic acid sequences and/or polypeptides encoded thereby which are essential for the viability of said microorganisms comprises comparative genomics. Furthermore, a particularly preferred embodiment relates to a method, wherein comparative genomis comprises the identification of orthologs. The term "orthologs" as used herein means nucleic acid sequences that are related by vertical descent from a common ancestor by species diversification and may encode proteins with the same or a similar function in different species. Usually, orthologs retain the same function in the course of evolution. However, orthologous genes may or may not be responsible for a similar function (for review see the glossary of the "Trends Guide to Bioinformatics", Trends Supplement 1998, Elsevier Science). Orthologous genes, nucleic acids or proteins comprise genes, nucleic acids or proteins which have one or more sequences or structural motifs in common, for example protein binding boxes or structure forming boxes. The sequence motifs of proteins can comprise short, i. e. repetitive sequences or amino acid positions conserved in the primary structure and/or conserved in higher protein structures, e. g., secondary or tertiary structure. Methods like BLAST searches for the identification of a candidate ortholog of a gene or a polypeptide are known to those skilled in the art.

Having defined a nucleic acid sequence, a polypeptide encoded thereby and/or an ortholog which is responsible for the viability of a microorganism, can be further investigated as a drug target. The term "drug target" as used herein comprises nucleic acids, polypeptides, orthologs, regulatory sequences and/or fragments thereof. For target prioritization, comparative genomics can be performed using the results of step (e). In case a nucleic acid sequence was identified and characterized as an obligatory essential gene, it can be translated into a sequence of amino acids. Nucleic acids and/or polypeptides sequences can be compared to other microbial amino acid sequences or to sequencs of eukaryotes, also humans, via data base search. Nucleic acid sequences and/or polypeptides encoded thereby which are found in many or all pathogens but not in eukaryotes are preferred targets for broad range antibiotics. Nucleic acid sequences and/or encoded polypeptides for which homologue and/or ortholog sequences are found in no or only a few other pathogens can selected as targets for narrow-range antibiotics. In accordance, another aspect of the present invention relates to the use of the method according to the invention for the identification and/or prioritization of drug targets in microorganisms.

As described, a novel method for the identification of obligatory essential microbial nucleic acid sequences is provided. Therefore, a further aspect of the present invention relates to a nucleic acid, obtainable by the method comprising an obligatory essential microbial sequence, particularly for the identification of an antimicrobial compound. Preferably, a nucleic acid sequence according to the invention comprises a coding sequence encoding at least tie mature form of a polypeptide or protein, i. e. the protein which is posttranslationally processed in its biologically active form, for example due to cleavage of leader or secretory sequences or a proprotein sequence or other natural proteolytic cleavage points.

In a preferred embodiment, the invention relates to a nucleic acid, comprising (a) a sequence derived form a region as shown in Table 3 or in Table 4 in operative linkage to 5 kbp upstream or downstream or preferably 1 kbp upstream or downstram to this region, the complement thereof or an ortholog or a protein coding fragment thereof, (b) a sequence of (a) comprising degeneration of the genetic code or (c) a sequence hybridizing under stringent conditions with one of the sequences of (a) and/or (b). Stringent hybridization conditions in the sense of the present invention are defined as those described by (Sambrook, 1989). According to this, hybridization under stringent conditions means that a positive hybridization signal is still observed after washing for 1 hour with 1×SSC buffer and 0.1% SDS at 55° C. preferably at 62° C. and most preferably at 68° C., in particular, for 1 hour in 0.2×SSC buffer and 0.1% SDS at 55° C., preferably at 62° C. and most preferably at 68° C.

In a still further aspect the present invention relates to an obligatory essential microbial nucleic acid, comprising (a) a sequence derived form a region as shown in Table 3 or in Table 4 in operative linkage to 5 kbp upstream or downstream or preferably 1 kbp upstream or downstream to this region, the complement thereof, an ortholog or a protein coding fragment thereof, (b) a sequence of (a) comprising degeneration of the genetic code or (c) a sequence hybridizing under stringent conditions with one of the sequences of (a) and/or (b).

Degeneration of the genetic code as used herein means any variation of the nucleic acid of which deviates in its primary structure, e. g., in sequence composition or in length as well as to ortholog components.

A plurality of obligatory essential nucleic acid sequences can be provided as an array, i. e. a plurality of sequences is provided on specific areas on a solid support, e.g., a nucleic acid chip. A further aspect of the present invention therefore relates to a nucleic acid array, comprising at least two of the nucleic acid sequences as described, preferably in an immobilized form. The arry may be used for diagnostic purposes or in a method for identifying new drugs.

In a still further aspect the present invention also relates to a vector, comprising at least one of the nucleic acid sequences described above or a corresponding fragment thereof. An other aspect of the invention therefore pertains to a cell, transformed with a nucleic acid or the recombinant vector as described. The cell may be a prokaryotic cell such as a Gram-negative or Gram-positive cell, or it can be an eukaryotic cell, such as yeast. Transformation of the conditionally replicating vector of the present invention representing chromosomal fragments of a microorganism of interest into a host cell results in a plurality of different transformants. Accordingly, a further aspect of the invention relates to a bank of transformants, comprising at least two microorganisms, transformed with a vector as described.

The method of the present invention provides means for the identification of obligatory essential nucleic acid sequences in microorganisms. Furthermore, it provides means for the identification and characterization of polypeptides or fragments thereof, encoded by said nucleic acids. An other aspect of the invention therefore relates to a polypeptide, (a) encoded by a nucleic acid sequence as described, a fragment or derivative thereof or (b) encoded by a sequence which is 60%, preferred 65% and particularly preferred 70% homologous to a nucleic acid sequence as described, a fragment or derivative thereof.

Percent (%) homology are determined according to the following equation:

$$H = \frac{n}{L} \times 100$$

wherein H are % homology, L is the length of the basic sequence and n is the number of nucleotide or amino acid differences of a sequence to the given basic sequence.

The terms "fragment" or "derivative" denotes any variant the amino acid deviates in its primary structure, e. g., in sequence composition or in length as well as to analogue components. For example, one or more amino acids of a polypeptide may be replaced in said fragment or derivative as long as the modified polypeptides remain functionally equivalent to their described counterparts.

One or more of the polypeptides as described may be complexed with one or more other polypeptides which may be homologous or heterologous polypeptides in vivo. Those proteins are called oligomers, and their single components are called subunits. An example for an heteromeric polypeptide is the *E. Coli* membrane-bound enzyme nitrate reductase which contains three subunits. Furthermore, metalloenzymes contain the inorganic cations as stably bound components of the enzyme complex.

Enzymes often are dimers or polymers consisting of homologous and/or heterologous proteins. Thus, only a native protein complex might have an enzymatic activity. To provide such a protein complex, monoclonal or polyclonal antibodies against one of the subunits of the complex can be generated. If antibodies are provided with an affinity tag, the protein complexed with other proteins can be separated from other cellular components by affinity chromatography. Therefore, complexes of polypeptides can be subjected to immunoprecipitation, e. g. with antibodies as described, in order to identify homologous or heterologous polypeptides which might be associated. Accordingly, another aspect of the invention relates to a complex of at least one polypeptide or a fragment thereof with at least one other polypeptide.

Another aspect of the present invention relates to an antibody which is specific for an aforementioned polypeptide or fragment thereof. Antibodies directed against a polypeptide as described may be prepared by any of a variety of methods using immunogens or epitopes of the polypeptide. Such immunogens include the full length polypeptide (which may or may not include the leader sequence) and fragments such as the ligand binding domain, the extracellular domain and the intracellular domain. These antibodies can be monoclonal antibodies, polyclonal antibodies or synthetic antibodies as well as fragments of antibodies, such as Fab+, Fv, F(ab')2, disulphide-bridged Fv or scFv fragments, etc. Monoclonal antibodies can be prepared, for example, by the techniques as original described in (Kohler, 1975), or in Harlow and Lane "Antibodies, A Laboratory Manual", CSH Press, Cold Spring Harbor, 1988.

A nucleic acid sequence as described can be directly used as a target for an antimicobial drug. A specific drug may bind to the essential nucleic acid and thereby functionally inactivate the nucleic acid, so that the affected microorganism is no longer viable and gets eliminated. Accordingly, a further aspect of the invention relates to the use of such a nucleic acid sequence as a drug target.

In order to identify drugs which are suitable as broad range antibiotics or rather to the contrary as narrow range antibiotics, the nucleic acid sequences can be used for the identification of corresponding targets in other microorganisms. This can be performed as described by comparative genomics. In accordance, still an other aspect of the present invention relates to the use of a nucleic acid for the identification of homologous nucleic acids in other microorganisms.

However, not only an obligatory essential nucleic acid sequence as described can be used as a drug target, but also a polypeptide which is encoded by the latter. The present invention therefore also relates to the is use of a polypeptide as a drug target. In accordance, a complex of at least one polypeptides with at least one other polypeptide can be an adequate target for drugs. Therefore, a still further aspect of the present invention relates to the use of a complex as described as a drug target.

In another aspect, the present invention relates to the use of an antibody for the identification of a drug target, wherein said drug target comprises at least one polypeptide or a fragment thereof as described, optionally complexed with at least one other polypeptide. As described, an antibody according to the invention can be used for immunoprecipitations in order to identify polypeptide complexes which are suitable as drug targets.

Genome saturating mutagenesis (GSM) as described in the present invention can be applied to any transformable organism with an effective recombination system. The term "genome saturating mutagenesis" as described before means that every gene or genomic nucleic acid sequence of an organism is targeted by mutagenesis at least once.

Using the method of the invention, every single locus is the target of insertional mutagenesis without any limitations concerning target sequence specificity. Accordingly, a further aspect of the present invention relates to a method for the identification of essential nucleic acid sequences comprising genome saturating mutagenesis.

Only recently, a negative approach was performed to identify essential nucleic acid sequences of the minimal Mycoplasma genome, whereby all viable transposon insertions were displayed on a Mycoplasma map. However, this approach is very resource intensive as discussed above, and obligatory essential nucleic acid sequences (sequences for which no viable transposon insertions can be found) were identified only indirectly.

To the contrary, applying GSM to an organism, a map of all sites of this organism can be obtained which are associated with cell viability and are therefore supposed to be part of obligatory essential nucleic acid sequences. Thus, the minimal genome of the investigated organism, preferably a microorganism, can be defined in vitro.

Using GSM as described in the present invention, several of the numerous bacterial genes without known function can be identified as obligatory essential nucleic acid sequences. Furthermore, using comparative genomics, several of them can be characterized as organism-specific, suitable for the selection as a target for narrow-range antibiotics.

In the present invention a novel method for the identification of obligatory essential nucleic acid sequences, in particular microbial sequences, and polypeptides encoded thereby is provided. The nucleic acids, polypeptides encoded thereby and/or corresponding complexes can be used as drug targets and/or for the identification of drugs. Another aspect of the invention therefore relates to a method for the screening and/or identification of an antimicrobial compound, wherein a nucleic acid sequence as described and/or polypeptide or corresponding fragment or derivative thereof is used. The term "compound" as used herein comprises both natural and synthetic molecules, nucleic acids such as antisense molecules, vectors comprising antisense molecules or nucleic acid sequences encoding an antagonist or inhibitor, cells comprising antisense molecules or nucleic acids encoding an antagonist or inhibitor, peptides, polypeptides, proteins, proteinaqueous or non proteinaqueous compounds and/or antibodies. Said compounds can be functional derivatives or analogues of known inhibitors or antagonists. The term "antagonist" or "inhibitor" as used herein means naturally occurring and synthetic compounds capable of counteracting with or inhibiting the activity of a nucleic acid sequence, preferably a gene or gene product, or interactions of the gene or gene product with other genes or gene products or counteracting with or inhibiting the activity of a polypeptide or complex of polypeptides.

Compounds or plurality of compounds can be identified from large libraries of both natural product and synthetic (or semi-synthetic) extracts or chemical libraries according to methods known in the art. The term "plurality of compounds" is to be understood as a plurality of compounds which may or may not be identical.

Those skilled in the art know that the precise source of test extracts or compounds is not critical to the screening procedure of the invention. Numerous methods are available for generating random or directed synthesis of any number of chemical compounds, including, but not limited to, saccharide-, lipid-, peptide-, and nucleic acid based compounds.

Natural and synthetically produced libraries can be produced according to methods known in the art, e. g. by standard extraction, fractionation and purification methods resulting in the careful characterization and identification of a chemical entity within a crude extract having the desired activity. Furthermore, if desired, any library or compound is readily modified using standard chemical, physical, or biochemical methods.

A preferred embodiment of the present invention relates to a method, comprising the steps (a) providing an obligatory essential nucleic acid sequence, an ortholog and/or polypeptide encoded thereby and (b) identifying a compound capable of modulating the activity of the latter.

Modulating the activity of a nucleic acid sequence or a polypeptide encoded thereby means that its activity is at least reduced or preferably inhibited, either by annealing or direct binding or by annealing or binding to a corresponding complex consisting of at least one of the polypeptides. In order to identify a compound fulfilling this requirement by drug discovery, a obligatory essential nucleic acid sequence, orthologs and/or polypeptides encoded thereby can be used as target compound.

Screening technologies are enzymatic, cell-based, reporter-gene or radio-ligand assays. Other technologies are filter binding assays, "real time" measuring of interaction using, for example, the BIAcore apparatus (Pharmacia), or fluorescence correlation spectroscopy (FCS). All these methods can be used in accordance with the present invention to identify specific compounds capable of modulating the activity of one or more nucleic acid sequences or encoded polypeptides as described.

Any molecule from the above described compound libraries can be screened by contacting the nucleic acid and/or the polypeptide or a corresponding fragment thereof with one or more test compounds.

Contacting means that a compound screening is performed, providing appropriate conditions to allow and measure any interaction between compounds and targets.

It is well known to a person skilled in the art that several technologies are available to perform compound screening, and compound libraries from different sources can be tested against targets from this invention. Target molecules can be prepared for compound screening in multiple forms, e. g. nucleic acids can be bound to filter membranes. Corresponding polypeptides of nucleic acids from this invention can be provided with one or more tags to allow purification by affinity chromatography or to allow binding of targets to magnetic particles loaded with nickel-nitrilotriacetic acid (Ni:NTA).

Display-systems can be used to identify surrogate ligands for a given target (Loferer, 2000). Surrogate ligands are short peptides that bind with high affinity to a target protein inhibiting its function. Examples for display-systems are DsbA (PCT/EP 94/02486) or the autotransporter system AIDA (WO97/35022). Polypeptides as described herein are translocated as passengers of a transporter protein across the the inner and outer membrane and exposed on the outer membrane. Immobilized target proteins are contacted with clonal bacterial cells displaying a peptide library. Cells with high affinity to the respective target are isolated, and the primary sequence of the high-affinity binding peptide can be obtained.

In a different approach using phage display, randomized peptides are displayed from phages and screened by affinity chromatography to an immobilized receptor (WO 91/17271, WO 92101047).

Binding studies as described above can be performed as "high-throughput screening". It is well known in the art that either the presented polypeptides or tie compounds or polypeptides have to be linked to a tag (e. g. a chromatophor) that enable detection and quantification of binding activities. Using a solid phase system, either the investigated polypeptide or cell or compound library or combinatorial library is bound to a coated surface. Binding of one component to the immobilized component can be detected by, for example, scintillation proximity assays (SPA), fluorescence polarization, or surface plasmon resonance (SPR).

In accordance with the above, a further preferred embodiment of the present invention relates to a method, comprising the steps (a) providing an obligatory essential nucleic acid sequence, an ortholog and/or polypeptide encoded thereby and (b) identifying a compound capable of modulating the activity thereof, wherein step (b) comprises:
(i) contacting the nucleic acid and/or the polypeptide or a corresponding fragment thereof with one or more test compounds and
(ii) determining whether said test compounds binds to said nucleic acid or said polypeptide.

Bacteria, for which it was shown that a nucleic acid sequence and/or polypeptide is encoded thereby is obligatory essential as described herein, can be used in a proliferation assay to identify both ligands and potential antagonists or inhibitors to said nucleic acids and/or polypeptides. Methods to determine growth and proliferation of bacteria are well known in the art, for example in Drews, Mikrobiol. Praktikum, Berlin, 1976.

Thus, a further preferred embodiment of the present invention relates to a method, comprising the steps (a) providing an obligatory essential nucleic acid sequence, an ortholog and/or polypeptide encoded thereby and (b) identifying a compound capable of modulating the activity thereof, wherein step (b) comprises:
(i) contacting a bacterial cell with one or more test compounds and
(ii) determining whether said contacting leads to cell growth inhibition and/or cell death.

A compound, shown to contact or bind to the nucleic acid and/or the polypeptide encoded thereby as described might be an antagonist or inhibitor of the activity of the latter.

As has been described, an obligatory essential nucleic acid can serve as a target for an antagonist or inhibitor. Antagonists may comprise of, for example, polypeptides that bind to the mRNA of said gene, thereby destabilizing the native conformation of the mRNA and disturbing the transcription and/or translation.

Potential antagonists/inhibitors further include antisense molecules. Antisense technology is well known in the art and discussed, for example, in Okano, 1991; Oligodeoxynucleotides as Antisense Inhibitors of Gene Expression, CRC Press, Boca Raton, Fla. (1988). Triple helix formation is discussed in, for instance, Cooney, 1988.

As indicated, an antagonist or inhibitor may be a polyclonal or monoclonal antibody according to the the present invention. Antibody production is well known in the art.

A compound useful as an antagonist or inhibitor of the activity of an essential nucleic acid sequence and/or polypeptide encoded thereby as defined above provides the key for an antimicrobial therapy since the antagonist or inhibitor stops or reduces bacterial growth and/or mediates bacterial death. Said compound may prove useful as a pesticide, and/or antibiotic. A preferred embodiment of the invention therefore relates to a method, wherein said compound is an antagonist or inhibitor.

In a further preferred embodiment, the present invention relates to a method, wherein said compound is further modified, e. g., by peptidomimetics or by applying phage display or combinatorial library techniques.

Peptidomimetics, phage display and combinatorial library techniques are well known in the art and can be applied by the person skilled in the art without further ado to the improvement of the antagonist or inhibitor that is identified by the basic method referred to herein above with the help of computer modelling, chemical derivatization and other.

Biological assays as described above or other assays such as assays based on crystallography or NMR may be employed to assess the specificity or potency of the antagonist or inhibitor wherein the decrease of one or more activities of the polypeptide may be used to monitor said specificity or potency. All techniques employed in the various steps of the method of the invention are conventional or can be derived by the person skilled in the art from conventional techniques without further ado.

Finally, the antagonist or inhibitor can be modified to improve its binding affinity or its potency and specificity by means well known in the art. If, for instance, there are electrostatic interactions between a particular residue of an polypeptide and some region of an antagonist or inhibitor molecule, the overall charge in that region can be modified to increase that particular interaction.

In accordance with the above, in a further aspect the present invention also relates to a compound, obtainable by the method as described. A preferred embodiment relates to a compound, comprising specific binding to one or more of the nucleic acids and/or to a polypeptide or fragment encoded thereby as described. According to the method, in a further preferred embodiment the compound is capable of reducing microbial growth and/or causing microbial death.

In order to screen and/or identify an antimicrobial compound according to the invention, in another aspect a kit can be provided which contains one or more obligatory essential nucleic acid sequences and/or one or more polypeptides encoded thereby and additionally one or more compounds.

In a further aspect, the present invention relates to a composition comprising as active agent either a nucleic acid or a vector or a cell or an antibody or a compound according to the invention. As is evident from the above, said composition comprises at least one of the aforementioned antagonists or inhibitors.

The term "composition", as used herein, comprises at least one small molecule or molecule as identified above, which can be a compound a polypeptide, an antigenic fragment of said polypeptide, a fusion protein, a nucleic acid sequence, a vector and/or a cell containing a nucleic acid sequence according to the invention and/or an antibody as described. The composition may be in solid, liquid or gaseous form and may be, inter alia, in form of (a) powder (s), (a) tablet (s), (a) solution (s) or (an) aerosol (s).

The active agents of the invention appear to function against nucleic acid sequenences or gene products which are obligatory essential in several strains or genera of bacteria. Accordingly, they may be used to slow, stop, or reverse bacterial growth of a wide spectrum of bacteria and can be formulated for therapeutic use as pharmaceutical compositions. The compositions can include, depending on the formulation desired, pharmaceutically acceptable, usually sterile, non-toxic carriers or diluents, which are defined as vehicles commonly used to formulate pharmaceutical compositions for animal or human administration. Those diluents or carrier are well known in the art. Thus, a preferred embodiment of the present invention relates to a composition for pharmaceutical use, optionally in a physiologically acceptable diluent or carrier.

The pharmaceutical composition of the invention can comprise further agents such as interleukins, interferons and/or CpG-containing DNA stretches, depending on the intended use of the pharmaceutical composition. In another preferred embodiment, the present invention therefore relates to a pharmaceutical composition, comprising one or more further active ingredients for simplifying or supporting the treatment of bacterial infections or disorders or diseases related to bacterial infections, such as an antibiotic and/or cytokine.

In accordance with the above, a further aspect relates to the use of an composition for the prevention and/or therapy of microbial infections. Furthermore, in a preferred embodiment the invention relates to the use of a compound, compris-
ing the inactivation and/or death of microorganisms by modulating the activity of obligatory essential nucleic acid sequences or polypeptides encoded thereby. Accordingly, the invention also relates to a method for treating or preventing bacterial infections or diseases or disorders related to bacterial infections comprising the step of administering to a subject in need thereof an antagonist or inhibitor identified herein above, optionally comprised in a pharmaceutical composition as described.

The following examples serve to explain the method of the invention in more detail, without implying any limitations.

EXAMPLES

Construction of a Random PCR Fragment Library (Froussard, 1992) using a Temperature-Sensitive Plasmid pIDM001 (Fuchs, 2001)

Chromosomal DNA is prepared as described (Sambrook, 1989). Genome-representing fragments are generated by Klenow enzyme with the chromosomal DNA as a template using random primer as described in Froussard, 1992; Patent Application WO 00/73502, or others. PCR primer are designed which are identical to the non-random 5'-stretch of the random primer, and PCR amplification using purified Klenow-fragments as template is performed. Generated fragments of 350-500 base pairs length are eluated, KpnI-restricted, and purified with a GFX DNA preparation kit. Restricted fragments are ligated with dephosphorylated, KpnI-restricted vector pIDM001 (FIG. 5) for 2.5 hours at 24° C. Ligated DNA is transformed into repA-wildtype strain EC101 and grown under permissive temperature (30° C.) in the presence of 17.5 µg/ml tetracycline for three days to a diameter of 2 mm. Plasmid-DNA from these clones is isolated using the GFX plasmid preparation kit.

Transformation of S. enterica ssp. Typhimurium

Plasmid-DNA is transformed into S. enterica ssp. Typhimurium. For this purpose, cells of S. enterica ssp. Typhimurium are prepared as described by (Sambrook, 1989) An aliquot of these "competent cells" is transformed with 100 ng of the plasmid DNA described in (a) (Sambrook, 1989). Transformed cells are appropriately diluted and plated on agar plates containing rich medium with tetracyclin (17.5 µg/µl).

Insertional Duplication Mutagenesis by Homologous Recombination

Insertional duplication mutagenesis by homologous recombination occurs during bacterial growth. Colonies grown after 56 h at permissive temperature are isolated into 96 well containing 200 µl LB-medium (tetracyclin 17.5 µl/ml). Cells are vortexed carefully.

Identifying Lethal Integrants by Replica Plating and Characterizing Lethal Integrants by Nucleic Acid Amplification 15-17 µl of the bacterial suspension are dropped on LB agar plates containing 17.5 µg/ml tetracycline, followed by incubation at 38.5° C. for 24 h. Colonies without viable genotype are characterized further by PCR using two plasmid specific primers which bind at both sides of the cloning site of the vector. The sequences of the two primers are, 5'-ataccgtcgac-ctcgag-3' and 5'-ccatggaagagcgcccaatacg-3'. PCR is performed using an appropriate aliquot of the cell suspension as a template. PCR is performed as follows: 95° C., 5'; 95° C., 30", 53° C., 30", 72° C., 40", 35 cycles. Clones with a positive signal (insert) are streaked out on LB agar plates and incubated for 48 h at 30° C. The integration rate per cell is determined by plating appropriate dilutions of a single colony on two series of LB agar plates (17.5 µg/ml tetracycline) followed by incubation at permissive (30° C.) and non-permissive temperature (37° C.). Master microtiter plates are incubated for 30 h at 30° C., and glycerin is added to a final concentration of 10-20%. Finally, the plates are softly vortexed and stored at −80° C.

Target Identification

Examples for target identification are listed in Table 2. PCR-amplified fragments from (d) are purified by GFX-columns (Pharmacia) and sequenced using primers that start near the cloning site of the fragments. Two primers are used for sequencing: a) 5'-gggaacaaaagctgggtacc-3'; b) 5'-atgaccatgattacgccaagc-3'. The obtained sequence is analyzed for vector-specific and fragment-specific nucleotides. Only fragment specific nucleotide sequences are devised to data analysis using the following data bases: Genome Sequencing Center National Center for Biotechnolociv Information Sanger Institute Blast searches using the above mentioned data bases are performed with the sequences 9.83, 13.17, 14.65 and 27.13 to identify homologous nucleotide sequences. All sequences are compared to the *Salmonella enterica* ssp. Typhimurium. (Table 2), *S. typhi* and *E. coli* genome sequence, respectively. Table 2 defines the part of a *Salmonella enterica* ssp. Typhimurium subgenomic sequence to which the sequenced fragment is identical or nearly identical (insertion). Thus, the gene complex and gene organization of a *Salmonella enterica* ssp. Typhimurium subgenomic fragment where a lethal insertion has taken place is identified.

Next, the targeted ORF is identified as well as the operon structure in accordance to the annotations of the *Salmonella enterica* ssp. Typhimurium, *E. coil* or *S. typhi* genomes (Table 2: operon). In addition, the translated sequence of any putative ORF deduced from the sequenced fragment including its flanking regions is compared to the data bases. Identified homologies and operon structures deduced from annotated sequences and/or from experimental studies are stored. Other insertional mutants within the same operon are taken into consideration to identify the obligate essential gene within a gene complex (Table 2: essential gene and classification).

To identify homologous proteins or domains, the amino acid sequences of the identified obligatory essential nucleic acid sequences are compared to other microbial or eukaryotic genomes using the above mentioned databases (Table 2: homologies).

TABLE 2

Target identification as described in the text.

| No. | Insertion | Operon | Essential gene | Classification | Homologies |
|---|---|---|---|---|---|
| 27.13 | O1: 93089–93221; E1: 2866–2998; C1: 537965–538097 | P > yifB | yifB: putative 2-component regulator | regulator | highly conserved among bacteria, non-human. 28 homologous with an E-value <4E−35; lowest: identity 41%, positive 58% |
| 14.65 | E2A: 145240–145404 | P > yigI-rarD | rarD: integral membrane protein | cell envelope | highly conserved among bacteria, non-human. 18 homologous with an E-value <4E−17; lowest: identity 25%, positive 47% |
| 13.17 | B2B: 215228–215530 | P > yciR | yciR | unknown function | highly conserved among bacteria, non-human. 90 homologous with an E-value <5E−32; lowest: identity 30%, positive 57% |
| 09.83 | B2B: 20473–20734 | | B1525; putative aldehyde dehydrogenase | dehydrogenase | highly conserved among bacteria, human. |

Tables 3 and 4: Insertion Sites.

Table 3:

Fragments from screening described above were sequenced. Length of sequenced fragments are ~100-400 bp. The obtained sequences were compared with the *Salmonella enterica* serovar Typhimurium sequence using a BLAST search program (http :/genome.wustl.edu/gsc/Blast/client.pl).

The first column refers to the number of the sequence.

The region of the *Salmonella enterica* serovar Typhimurium genome sequence which is identical or nearly identical (>95%) to the cloned fragment is called insertion. Its beginning and ending is defined by the second and third column, respectively.

The orientation of the cloned fragment within the vector is described by the fourth column. "0" means that the lac promoter is in front of the start of the insertion and "1" vice versa. The fifth column depicts the gene or gene complex which is affected by the homologous recombination.

Table 4:

In Table 4 supplemental data from the screening procedure are disclosed.

TABLE 3

| Number | insertion: start | insertion: stop | orientation | affected gene |
|---|---|---|---|---|
| 037.37 | 0012931 | 0013331 | 0 | dnaK (11593-13509): chaperone Hsp70; DNA biosynthesis, autoregulated, heat shock proteins; chaperone Hsp70 in DNA biosynthesis/cell division (1st module) |
| 048.07 | 0019501 | 0019901 | 1 | virulenzplasmid; 19420-18899 ?: S. typhimurium hypothetical 11.3 KD protein (GB: Y18434) |
| 053.37 | 0055517; 0055228: 0055111 | 0055917; 0055628; 0055511 | 1;; 1 | ileS (53855-56689): isoleucine tRNA synthetase |
| 001.63 | 0069970 | 0070370 | 0 | CitE (70000-70869); Citrat-Lyase; operon STM unklar; |
| 019.09 | 0107431; 0107113 | 0107831; 0107513 | 1; 0 | imp (105810-108170): Organic solvent tolerance protein precursor; operon? P > imp-surA-pdxA-ksgA-apaG; polar effect on surA, essential for survival in stationary phase |
| 017.76 | 0142623; 0142499 | 0143023; 0142899 | 1; 1 | ftsI, cell division, septum formation, penicillin-binding protein 3; peptidoglykan-synthetase |
| 008.92 | 4599589 | 4599989 | 0 | YjeE (4599871-4600332)-yjeF (4598352-4599899); hypothetische Proteine; P > yjeF-yjeE-amiB-mutL (amiB: N-acetylmuramoyl-L-alanine-amidase), s. 10.36; polar effect?; paper Freiberg |
| 067.80 | 4611503 | 4611903 | 0 | vacB (4611048-4613486) |
| 066.67 | 4636387 | 4636787 | 0 | ytfE (4636353-4637015) |
| 026.79 | 4651369 | 4651769 | 1 | ytfP (4651549-4651893); ytfN (4647767-4651546) truncated? |
| 067.29 | 4670607 | 4671007 | 1 | orf (4670344-4671177); truncated? |
| 116.68 | 4714018 | 4714418 | 1 | miaE (4713327-4714139); ygtA (4714373-4714861) (1) |
| 090.30 | 4715929 | 4716329 | 1 | yjgN (4715666-4716853); Nahe tRNA synthetase |
| 047.37 | 4802826 | 4803226 | 0 | DnaC (4802774-4803511), DNA biosynthesis; initiation and chain elongation" |
| 067.78 | 4856084 | 4856484 | 0 | yjjl (4856163-4856303), lasT (4856703-4857389); putative tRNA/tRNA methyltrans-ferase; orf046, creC-creD-Terminator-dye-orf046 < P-P > (*E. coli*) |
| 064.57 | 3199611 | 3200011 | 1 | lysS (3199208-3200725): lysine tRNA synthetase; P > prfB-lysS |
| 038.81 | 3201158; 3201404 | 3201558; 3201804 | 0; 0 | prfB (3200735-3201616): peptide chain release factor RF-2; P > prfB-lysS |
| 107.77 | 3246136 | 3246536 | 0 | kein orf, zw. 7 orf (spezifisch) v. 3240633-3248772) |
| 142.56 | 3252003 | 3252403 | 0 | metK (3251682-3252836): methionine adenosyltransferase 1 (AdoMet synthetase) |
| 007.21 | 3369382 | 3369782 | 1 | Cca (3369210-3370451); tRNA nucleotidyl transferase; aminoacyl tRNA synthetases, tRNA-modification |
| 142.79 | 337296 | 337751 | 1 | orf (337095-337835); homolog-455 bp!; BLAST shows homology to two flanking genes! |
| 123.48 | 3377195 | 3377595 | 0 | rpoD (3376390-3378237): sigma D (sigma 70) factor of RNA polymerase, major sigma factor during exponential growth (2nd module) |
| 087.44 | 3447439 | 3447839 | 0 | csdA (deaD)(3446174-3448114); cysteine sulfinate desulfinase; RNA synthesis, modification, DNA transcription; inducible ATP-independent RNA helicase; P > csdA-mtr?; mtr |
| 062.51 | 3448153 | 3448553 | 0 | yhbM (3448242-3449126); verm. polarer Effekt, s. o. |
| 004.39 | 3453905; 3454941; 3455663 | 3454305; 3455341; 3456063 | 1; 0; 1 | infB (3453599-3456277): protein chain initiation factor; P > infB? |
| 076.95 | 3457013; 3456460 | 3457413; 3456860 | 0; 0 | nusA (3456302-3457804): RNA synthesis, DNA-transcription; P > yhbC-nusA-infB |
| 087.39 | 3464882 | 3465282 | 0 | hflB (3464679-3466613): ATP-dependent zinc-metallo protease (2nd module); Operon? |
| 006.50 | 3470878 | 3471278 | 0 | yhbZ (3470208-3471380); hypoth. GTP- |

TABLE 3-continued

| Number | insertion: start | insertion: stop | orientation | affected gene |
|---|---|---|---|---|
| | | | | bindendes Protein; P > yhbE-yhbZ? S. Loferer |
| 078.78 | 3566955 | 3567355 | 1 | rrfD (3566856-3566977) |
| 059.60 | 3567367; viele weitere | 3567767 | 1; 1 | rrlD (3567067-3570060) |
| 065.88 | 3571505 | 3571905 | 1 | rrsD (3570452-3571995); 16S rRNA |
| 089.82 | 3583496 | 3583896 | 1 | rpoA (3583289-3584278): RNA polymerase alpha subunit |
| 051.65 | 3585134 | 3585534 | 1 | rpsM (3585364-3585720); 30S ribosomal subunit protein S13; -rpsK (3584958-3585347): 30S ribosomal subunit protein S11 |
| 090.44 | 3585847 | 3586247 | 0 | rpmJ (3585867-3585983): 50S ribosomal subunit protein X; -secY (3586015-3587346): preprotein translocase of IISP family, membrane subunit, putative ATPase |
| 052.28 | 3586056; 3586043; 3586421; 3586576; 3586604; etc | 3586456; 3586443; 3586821; 3586976; 3587004 | 1; 0; 0; 0; 1; 0; 0; 1 | secY (3586043-3587346); |
| 032.53 | 3587321; 3587305; 3587357; 3587362; 3587372; | 3587721; 3587705; 3587757; 3587762; 3587772; | 0; 1; 1; 0; 1; 1; 0 | rplO (3587354-3587788): 50S ribosomal subunit protein L15: ribosomale Proteinsynthese + Promotorregion prlA (putative ATPase subunit of translocase) ov prom prlA |
| 112.89 | 3587624 | 3588024 | 1 | rpsE; rpmD (3587792-3587971) |
| 076.30 | 3588100; 3588175 | 3588500; 3588575 | 1; 1 | rpsE (3587975-3588478): 30S ribosomal subunit protein S5 |
| 067.03 | 3588867 | 3589267 | 0 | rplF (3588856-3589389), 50S ribosomal subunit protein L6 |
| 111.66 | 3590030 | 3590430 | 1 | rplE (3590148-3590687) |
| 013.25 | 3592116 | 3592516 | 1 | rplP (3592007-3592417); 50S ribosomal subunit protein L16 |
| 141.60 | 3592250 | 3592650 | 0 | rplP: 50S ribosomal subunit protein L16; rpsC |
| 089.84 | 3594291 | 3594691 | 0 | rplB (3593791-3594612); 50 S ribos. Protein L2 |
| 070.33 | 3595397 | 3595797 | 0 | rplD (3594929-3595534): 50S ribosomal subunit protein L4 |
| 001.78 | 3595405; 3595423; 3595668 | 3595805; 3595823; 3595068 | 0; 1; 0 | rplC (3595545-3596174): 50S ribosomal subunit protein L3; ov rplC/rplD |
| 02.83 | 3600536 | 3600936 | 0 | fusA (3599546-3601660); -tufA |
| 032.43 | 3601973 | 3602373 | 0 | rpsG (3601757-3602227): 30S riboasomal subunit protein S7 |
| 045.37 | 3601994 | 3602394 | 0 | rpsG-rpsL (30S ribosomal subunit protein S12); ov |
| 017.03 | 3620872 | 3621272 | 0 | Fic (3620342-3620944): putative cell filamentation protein, stationary phase induced gene, affects cell division |
| 107.01 | 3739529 | 3739929 | 0 | ftsY (3738734-3740209): GTPase domain of cell division membrane protein |
| 003.40 | 3840048 | 3840448 | 1 | glyS (3839758-3841827), Beta-UE der Glycin-tRNA-Synthetase, Operon mit glyQ |
| 079.54 | 3841932 | 3842332 | 1 | glyQ (3841837-3842748): glycine tRNA synthetase, alpha subunit |
| 048.42 | 3908804 | 3909204 | 1 | rfaL (3908278-3909492), O-antigen ligase: P > rfaD-rfaF-rfaC-rfaL; polar effect on rfaD (essential)? |
| 130.60 | 3915002 | 3915402 | 0 | rfaB (3914522-3915601): UDP-D-galactose: (glucosyl)lipopolysaccharide-1,6-D-galactosyltransferase (2nd module) |
| 084.23 | 3919537 | 3919937 | 1 | kdtA (3919326-3920603); 3-deoxy-D-manno-octulosonic-acid transferase (KDO transferase); kdtB essential |
| 113.44 | 3924013; 3924053; 3924231 | 3924413; 3924453; 3924631 | 0; 0; 0; 0 | dfp (3923506-3924729): flavoprotein affecting synthesis of DNA and pantothenate metabolism; DNA - replication, repair, restriction/modification |
| 075.63 | 4039553; 4040395; 4040298; 4040749 | 4039953; 4040795; 4040698; 4041149 | 0; 1; 1; 1; 1 | gyrB (4038843-4041257): DNA replication, repair, restriction, modification; P > recF-gyrB |

TABLE 3-continued

| Number | insertion: start | insertion: stop | orientation | affected gene |
|---|---|---|---|---|
| 140.40 | 4041401 | 4041801 | 1 | recF (4041286-4042359): gap repair protein; operon mit gyrB (essential) |
| 063.31 | 4046410 | 4046810 | 0 | yidD (4046153-4046410): hypothetical protein: 60iM (4046413-4048059) 60 kD inner membrane protein, P > yidD-thdF? |
| 062.24 | 4063750 | 4064150 | 0 | pstS (4063573-4064613): ABC superfamily (bind_prot), high-affinity phosphate transporter |
| 065.88 | 4100234 | 4100634 | 0 | rrsC, rrsE, rrsB, rrsA, rrsH, rrsD, rrsG |
| 075.66 | 4102455; 4102485; 4103161; 4103533; viele weitere | 4102855; 4102885; 4103561; 4103933 | 0; 00; 0 | rrlC(4104028-4105007) |
| 027.13 | 4106905 | 4107305 | 0 | yifB (4106851-4108371): putative 2-component regulator, P > yfiB-x < P |
| 132.58 | 4120506 | 4120906 | 0 | rep (4119751-4121775): Rep helicase, a single-stranded DNA dependent ATPase (1st module) |
| 002.74 | 4124626 | 4125026 | 1 | TrxA (4124822-4125151): cytoplasmic thioredoxin. Biosynthesis of cofactors, carriers: thioredoxin, glutaredoxin, glutathione und/oder downstream rhlB: RNA-Helicase |
| 063.51 | 4183740; 4184136 | 4184140; 4184536 | 1; 0 | yigC (4183584-4185062): putative oxidoreductase; P > yigC-ubi8; polar effect on rfaH? |
| 065.88 | 4196161 | 4196561 | 0 | rrsA (4196045-4197586): 16S rRNA |
| 075.66 | 4198543 | 4198943 | 0 | rrlA (4198102-4200113): 23S rRNA |
| 064.65 | 4206439 | 4206839 | 1 | polA (4206117-4208903): DNA polymerase I |
| 131.34 | 4216712 | 4217112 | 0 | orf (4216973-4217401); glnA (4215585-4216994) |
|  | 4319806 | 4320206 | 1 | katG (4319569-4321749): catalase; hydroperoxidase HPI(I) |
| 065.88 | 4351232 | 4351632 | 0 | rrsB (4351116-4352659) |
| 060.10 | 4353644 | 4354044 | 0 | rrl |
| 063.96 | 4355109 | 4355509 | 0 | rrlB (4355270-4356166): 23S rRNA |
| 139.24 | 4357278 | 4357678 | 0 | murB (4356658-4357686): UDP-N-acetylenolpyruvoylglucosamine reductase |
| 066.11 | 4365223 | 4365623 | 1 | rplL (4365211-4365576), *Salmonella typhimurium* 50S ribosomal protein L7, rplJ-rplL-rpoB-rpoC (STM) |
| 064.84 | 4365936; 4365955; 4367326; 4368581; 4368628 | 4366336; 4366355; 4367726; 4368981; 4369028 | 1; 0; 0; 0; 1; 1 | rpoB (4365894-4369922): RNA-Polymerase beta UE; P > rpoB-rpoC |
| 062.03 | 4370453 | 4370853 | 0 | rpoC (4369999-4374222): RNA polymerase beta subunit, P > rpoB-rpoC |
| 073.34 | 4384326; 4384393; 4384774 | 4384726; 4384793; 4385174 | 1; 0; 0 | hemE (4384131-4385195); uroporphyrinogen decarboxylase, P > yjaD-hemE-nfi-yjaG-P > |
| 065.88 | 4394777 | 4395177 | 0 | rrsE (4394661-4396205): 16S rRNA |
| 075.66 | 4397038 | 4397438 | 0 | rrlE (4396597-4398608): 23S rRNA |
| 062.23 | 4399002; 4399188 | 4399402; 4399588 | 0; 0 | rrlX: 23S ribosomal RNA |
| 010.49 | 4479697 | 4480097 | 1 | spi4_c (4479849-4481168); ABC exporter outer membrane component homolog? |
| 041.27 | 4500041 | 4500441 | 1 | Spi4_R = LtkB: ABC-transporter, leukotoxin expression protein B; operon |
| 059.26 | 4517808 | 4518208 | 0 | NrfB: formate-dependent nitrite reductase; a penta-haeme cytochrome c; P > nrfABCDEFG |
| 132.25 | 4575579 | 4575979 | 1 | mopA (4575096-4576742): chaperone Hsp60 with peptide-dependent ATPase activity, affects cell division |
| 121.51 | 4586654 | 4587054 | 0 | yjeA (4586080-4587057): putative pyruvate oxidase (lysyl-tRNA synthetase) |
| 043.60 | 0144044 | 0144444 | 1 | murE, meso-diaminopimelate-adding enzyme |
| 118.75 | 0147040 | 0147440 | 0 | mraY (146315-147397): phospho-N-acetylmuramoyl-pentapeptide transferase |
| 096.50 | 0147461 | 0148716 | 1 | murD (147400-148716): UDP-N-acetylmuramoylalanine-D-glutamate ligase |

TABLE 3-continued

| Number | insertion: start | insertion: stop | orientation | affected gene |
|---|---|---|---|---|
| 048.68 | 0149596; 0149310 | 0149996; 0149710 | 1 | ftsW, murG. |
| 006.53 | 0150261 | 0150661 | 0 | murG |
| 086.08 | 0151299; 0151367; 0151731 | 0151699; 0151767; 0152131 | 1; 0; 1 | MurC(151143-152618): L-alanine adding enzyme, UDP-N-acetyl-muramate: alanine ligase; operon: P > murF-ftsl-murE-murF-P?-mraY-murD-ftsW-murG-murC-ddlB-PQ-ftsA-ftsZ |
| 125.85 | 0152611 | 0153531 | 0 | ftsA (0154360-0155622): ATP-binding cell division protein, septation process, complexes with FtsZ |
| 013.09 | 0153292 | 0153692 | 1 | ddlB; D-alanine-D-alanine ligase B, affects cell division; polar effect on transcription of ftsQ, ftsA, ftsZ |
| 118.37 | 0156014 | 0156414 | 0 | ftsZ (155883-156834): tubulin-like GTP-binding protein and GTPase, forms circumferential ring in cell division |
| 005.53 | 0180996; 0181176 | 0181396; 0181576 | 1; 1 | lpdA (181007-182431), Lipoamid-Dehydrogenase im 2-Oxodehydrogenase- u. Pyruvatkomplex, L-Prot; P > lpdA |
| 022.64 | 0198916 | 0199316 | 0 | gcd (198220-200610): glucose dehydrogenase; P > gcd |
| 133.23 | 0254990 | 0255390 | 1 | rpsB (0254297-0255022): 30S ribosomal subunit protein S2; tsf (0255280-0256131): protein chain elongation factor EF-Ts |
| 087.21 | 0263270; 0264092; 0263189; 0264247 | 0263670; 0264492; 0263589; 0264647 | 0; 0; 0 | yaeT (262379-264793): hypoth. Protein of unknown function; P > cdsA-yaeL-yaeT; polar effect on lpxD (essential)? |
| 053.52 | 0266981 | 0267381 | 1 | LpxA (266995-267783): UDP-GlcNAc acyltransferase; P > lpxA-lpxB-rnhB-dnaE (RNA polymerase III) |
| 119.18 | 0273170; 0273195; 0273297 | 0273570; 0273595; 0273697 | 0; 1; 0 | accA (273043-274002): acetylCoA carboxylase, carboxytransferase, component, alpha subunit; P > accA |
| 65.88 | 0289281 | 0289688 | 0 | rrsH (289189-290732): 16S rRNA |
| 75.66 | 0291661; viele weitere: s. Tab. 3 | 0292061 | 0; 1; 0 | rrlH (291244-294336): 23S rRNA |
| 045.43 | 0298049 | 0298449 | 1 | yafD (298240-299019); hypothetical protein, yafC-P > yafD-yafE |
| 040.95 | 0308111 | 0308511 | 1 | orf: 306723-308606; operon? P > orf-orf2 (305731-306726)-orf3 (304665-305720) |
| 001.11 | 0328412 | 0328812 | 1 | orf: 327730-328518, 328545-328931 |
| 017.53 | 0336058 | 0336458 | 0 | orf: 332551-336645 |
| 017.53 | 0337263; 0337338 | 0337463; 0337738 | 0; 1 | orf: 337095-337835 |
| 017.53 | 0339735 | 0340135 | 0 | orf: 340044-340352 |
| 141.87 | 0344954 | 0345354 | 1 | orf (0343566-0346076) |
| 015.89 | 0387213; 0388227 | 0387613; 0388627 | 1; 0 | orf: 387133-388683; operon? P > orf-orf (388783-389526)-orf (389499-389987) |
| 114.48 | 0389348; 0388794 | 0389748; 0389194 | 0; 1 | orf (388783-389526), orf (389499-389987) |
| 044.95 bzw. 44.85 | 0433005 | 0433405 | 1 | yaiY (432726-433034), yaiZ (433302-433517); yaiW (431594-432688)-nn(b0379)-P-nn(b0380)-ddlA-nn- |
| 053.54 | 0451218 | 0451618 | 0 | phoB (450795-451484)-phoR (451554-452849); P > phoB-phoR; survival in stationary phase |
| 019.33 | 0464647 | 0465047 | 1 | secF (464189-465160): protein secretion, membrane protein; P > yajC-secD-secF? |
| 023.96 | 0475748 | 0476148 | 0 | dxs (474630-476492): 1-deoxyxylulose-5-phosphate synthase Central intermediary metabolism: Pool, multipurpose conversions; P > ORF-ispA-dxs-yajO |
| 120.47 | 0493014 | 0493414 | 1 | orf (0491989-0493272) |
| 114.44 | 0494170 | 0494570 | 1 | cyoE (493354-494244): protohaeme IX farnesyltransferase (haeme O biosynthesis); cyoD (494256-494585): cytochrome o ubiquinol oxidase subunit IV; polar effect on orf? S. o. |
| 041.38 | 0504469 | 0504859 | 0 | ClpX (504085-505356): ATP-dependent specificity component of clpP serine protease, chaperone; P > clpP-clpX-P > lon |

TABLE 3-continued

| Number | insertion: start | insertion: stop | orientation | affected gene |
|---|---|---|---|---|
| 098.87 | 0529331 | 0529731 | 1 | acrB (529247-532396): RND family, acridine efflux pump; gyrB mutant |
| 140.25 | 0546815; 0547820 | 0547215; 0547220 | 1; 1 | hemH (0546914-0547876): ferrochelatase |
| 092.44 | 0597932 | 0598332 | 1 | lpxH (597742-598464): UDP-2,3-diacylglucosamine hydrolase |
| 127.23 | 0602850 | 0603250 | 0 | folD (0602701-0603567): bifunctional 5,10-methylene-tetrahydrofolate dehydrogenase and 5, 10-methylene-tetrahydrofolate cyclohydrolase; polar effect? |
| 006.91 | 0616098 | 0616498 | 0 | orf (614803-616455); Homologien zu cytochrom c oxidase, RNA helicase, oxidoreductase, permease |
| 138.14 | 0662114 | 0662514 | 1 | cstA (0661273-0663378): carbon starvation protein |
| 065.56 | 0667126 | 667526 | 1 | ybdN (666641-667876) |
| 130.42 | 0678014 | 0678414 | 0 | ybdR (678022-679260): putative dehydrogenase |
| 063.08 | 0708021 | 0708421 | 1 | holA (707488-708519): DNA-polymerase III delta subunit, P > leuS-rlpB-holA-ybeN? |
| 052.92 | 0731768 | 0732168 | 1 | ybeX (731729-732607): integral membrane; P > ybeY-ybeX-Int |
| 141.92 | 0829294 | 0829694 | 1 | orf (828570-829817) |
| 020.43 | 0878747 | 0879147 | 0 | YbhP (0)(878349-879107)): hypothetisches Protein, ybhN-ybhO-ybhP < P-ybhQ (879240-879650)-P-ybhR-yhiH |
| 049.22 | 0921086 | 0921486 | 1 | yliB (920004-921542); P > yliB-yliC-yliD |
| 016.91 | 0929106 | 0929506 | 1 | orf (928719-929882), AcylCoA-dehydrogenase, *Pseudomonas*: PA0879?? |
| 009.65 | 0931253 | 0931653 | 1 | orf (930394-932016) Oxidoreductase; flavoprotein ubiquinone oxidoreductase? |
| 136.34 | 0955409 | 0955809 | 1 | orf (954543-955868); P > orf-orf2-orf3 |
| 016.82 | 0960461 | 0960861 | 1 | ArtI (960293-961024): arginine 3rd transport system periplasmic binding protein; ABC transporter, P > artP-artI-artQ-artM..? |
| 025.70 | 1007534; 1007594 | 1007934; 1007994 | 0; 1 | ybjT (1007622-1009055): putative dTDP-glucose enzyme; orf-ybjT < P; polar effect? |
| 066.03 | 1027553; 1027512 | 1027953; 1027912 | 0 | ycaC (1027678-1028355); polar effect on serW (1027440-1027524): serin tRNA? |
| 088.15 | 1063508 | 1063908 | 0 | aroA (1062633-1063916): 3-enolpyruvylshikimate-5-phosphate synthetase; polar effect on heat shock protein ycaL? |
| 059.56 | 1070253; 1071631; 1070670 | 1070653; 1072031; 1071070 | 1; 0; 1 | MsbA (1070434-1072182): ATP-binding transport protein; ABC-transporter; multicopy suppressor of htrB; transport of small molecules; P > ycaI-msbA-lpxK-ycaQ-ycaR |
| 115.84 | 1074868 | 1075268 | 1 | kdsB (1074663-1075409): CTP:CMP-3-deoxy-D-manno-octulosonate transferase |
| 031.69 | 1078525; 1078916 | 1078925; 1079316 | 0; 1 | mukF (1078201-1079523): killing factor, cell division; P > smtA-mukF-mukE-mukB |
| 031.34 | 1092505 | 1092905 | 0 | asnS (1091478-1092878): Aminoacyl tRNA synthetases |
| 125.92 | 1095712 | 1096112 | 0 | orf (1095316-1096752) |
| 027.15 | 1101114 | 1101514 | 1 | recE (1100135-1101292), (1101255-1104140) exodeoxyribonuclease VIII recE; P > racC-recE-FUN? |
| 074.30 | 1113807 | 1114207 | 0 | orf: (1113934-1114446) keine Homologie zu *E. coli* |
| 011.14 | 1122016 | 1122416 | 0 | orf: 1120665-1122746 |
| 026.65 | 1184282 | 1184682 | 1 | copR 1183635-1184381); orf (1184451-1184861). b1970: transthyretin like protein precursor. Reductase. P > copR-copS |
| 087.94 | 1205128 | 1205528 | 1 | wrbA (1205221-1205817)-yccJ (1204973-1205200) |
| 007.19 | 1217392 | 1217792 | 1 | orf (1216439-1217935) |
| 083.80 | 1218315 | 1218715 | 1 | orf (1218272-1218952) |
| 057.54 | 1222717 | 1223117 | 0 | orf (1221639-1222919); orf (1222930-1224036) |

TABLE 3-continued

| Number | insertion: start | insertion: stop | orientation | affected gene |
|---|---|---|---|---|
| 112.65 | 1245246 | 1245646 | 0 | yceI (1244858-1245433); orf (1245430-1246002) |
| 017.28 | 1255734 | 1256134 | 1 | MviN (1254962-1256536); putative virulence factor (STM) |
| 035.26 | 1262791 | 1263191 | 0 | flgH (1262644-1263342), Operon mit weiteren Flagellen-Genen. P > flgBCDEFGHIJKL |
| 057.43 | 1262844 | 1263244 | 1 | flgH, flgI |
| 062.37 | 1274223 | 1274623 | 0 | yceF (1274489-1275073) |
| 105.01 | 1279415; 1279426 | 1279815; 1279826 | 0; 0 | fabG (1279221-1279955): 3-oxoacyl-reductase; P > plsX-fabH-fabD-acpP-fabF; fatty acid biosynthesis |
| 070.77 | 1282057 | 1282457 | 1 | pabC (1281798-1282607), 4-amino-4-deoxychorismate lyase; P > pabC-yceG-P-tmk (essential)-holB (essential)-ycfH; pabC-mutant requires PABA (p-aminobenzoate) |
| 008.77 | 1283645 | 1284045 | 0 | tmk (1283622-1284263); thymidylate kinase-replication |
| 059.17 | 1320672; 1320427; 1319485 | 1321072; 1320827; 1320855 | 0; 1; 0 | purB (1319485-1320855); adenylo-succinate lyase; ycfC (1320859-1321500). purB non-essential, trmU essential; polar effect?; s. a. lpxH (600K) |
| 088.92 | 1324663; 1324724 | 1325063; 1325124 | 1; 0 | icdA (1324383-1325633): isocitrate dehydrogenase in e14 prophage. specific for NADP+ |
| 045.18 | 1331865 | 1332265 | 1 | pagD (1331174-1331437); pagC (1332249-1332806) |
| 068.91 | 1337846 | 1338246 | 1 | orf (1337446-1337976); orf (1338125-1338439) |
| 070.35 | 1376224 | 1376624 | 0 | selD (1375600-1376649): selenophosphate synthase, H(2) Se added to acrylyl-tRNA; P > ydjA-selD-topB-(topoisomerase III); polar effect on topB |
| 121.64 | 1413982 | 1414382 | 0 | thrS (1412199-1414127): threonine tRNA synthetase (2nd module) |
| 011.81 | 1416693; 1416800; 1417262; 1418461 | 1417093; 1417200; 1417662; 1418861 | 1; 0; 1; 0 | PheT (1416674-1419061); phenylalanine tRNA synthetase, beta-subunit oder himA (DNA-Replikation); P > pheT-himA |
| 070.87 | 1449112 | 1449512 | 0 | ydiJ (1446501-1449557): putative paral oxidase; P > ydiJ-ybdB-ydiH |
| 072.74 | 1480919 | 1481319 | 1 | spiA (1480399-1481892); P > spiA |
| 065.40 | 1485585 | 1485985 | 0 | sseC (1484994-1486448); polar effect on sseD? |
| 113.67 | 1501147 | 1501547 | 1 | ssaU (1500428-1501486); upstream: tRNAVal; polar effect? |
| 014.38 | 1512482 | 1512882 | 0 | gloA (1512447-1512854): lactoylglutathione lyase; P > gloA-mt (RNase T, degrades tRNA, has exonuclease and ssDNAseactivity); polar effect on mt? |
| 028.89 | 1530500 | 1530900 | 1 | ydgO (1530508-1531566); polar effect? P > ydgO-ydgP-ydgQ-nth |
| 089.62 | 1550161 | 1550561 | 0 | ompN (1549673-1550806); P > ompN-FUN?; umgeben von regulatory system (ompR family) |
| 066.28 | 1591866 | 1592266 | 0 | yciG (1592069-1592251), ydfH-ydfG-P > dcp-yciG-P-ydcJ (STY) |
| 009.83 | 1601741 | 1602141 | 0 | yneI (1601178-1602566), B1525; putative succinate-semialdehyde dehydrogenase, P > b1525-P > |
| 014.07 | 1610755 | 1611155 | 1 | hyaD (1610683-1611291): hydrogenase 1 maturation protease; P > hyaA . . . hyaF |
| 098.42 | 1618929 | 1619329 | 0 | orf (1618315-1619601) |
| 119.17 | 1627904 | 1628304 | 1; 1 | orf (1627914-1628822): |
| 009.47 | 1633672 | 1634072 | 0 | orf (1633276-1634727); Hypothetischer Na/H-Antiporter; putatives Transmembran-Transportprotein; geringe Homologie |
| 125.26 | 1639682 | 1640082 | 1 | orf (1638187-1640715) |
| 024.31 | 1658266 | 1658666 | 1 | orf (1656805-1658292); orf (1658410-1658988); probable transcriptional regulator |
| 089.17 | 1664180 | 1664580 | 1 | narZ (1660683-1664423)-narY (1664420-1665964); narZ required for long-term starvation-survival |
| 011.48 | 1664856 | 1665256 | 0 | narY/narH: nitrate reductase beta-UE; |

TABLE 3-continued

| Number | insertion: start | insertion: stop | orientation | affected gene |
|---|---|---|---|---|
| | | | | narZYV, minor nitrate reductase; P > narU-narZ-narY-narW-narV-yddE? |
| 042.26 | 1727005 | 1727405 | 0 | orf (1726871-1728421) |
| 014.13 | 1731287 | 1731687 | 0 | hrpA (1731329-1735231): ATP-dependent Helicase; P > hrpA-ydcF; polar effect on ydcF? |
| 131.63 | 1741057 | 1741457 | 1 | hslJ (1741124-1741534): heat shock protein hslJ |
| 028.68 | 1757740 | 1758140 | 0 | orf (1757884-1758486) methyltransferase? |
| 136.26 | 1791749 | 1792149 | 1 | ycjE (1791714-1792013); fabI (1792131-1792919): enoyl-[acyl-carrier-protein] reductase (NADH); fabI essential |
| 013.17 | 1796398 | 1796798 | 1 | YciR (1796537-1798519); P > yciR; gegenstrang: ynaJ (1756761-1757798) |
| 068.19 | 1801641 | 1802041 | 0 | yciM (1801510-1802679), hyp. Heat shock protein, P > yciS-yciM-P > |
| 079.16 | 1843617 | 1844017 | 1 | adhE (1843123-1845801): CoA-linked acetaldehyde dehydrogenase and iron-dependent alcohol dehydrogenase; pyruvate-formate-lyase deactivase; P > adhE |
| 044.34 | 1850066; 1850477 | 1850466; 1850877 | 1; 1 | ychK (1850038-1850943): P > ychK-mviA? S. a. mviN |
| 079.93 | 1853277, 1853452, 1853103, 1852929 | | 0 | Nahe tyrT (1852565-1852646), tyrV (1852854-1852935): tyrosine tRNA; unklar |
| 089.17 | 1858271 | 1858671 | 0 | narH (1856876-1858411)-narG (1858408-1862151) |
| 007.22 | 1879280; 1879650 | 1879680; 1880050 | 1; 0 | YchM (1878852-1880513); hypothetical sulfate: proton symporter (S. typhi), unknown function; P > ychM-ychH < P |
| 077.32 | 1917904; 1918052 | 1918304; 1918452 | 0; 0 | yeaZ (1917760-1918455), P > yoaA-yeaZ-orf, Promoter-lacZ? |
| 008.66 | 1920897 | 1921297 | 0 | yoaH (1920904-1921083); P > pabB-yeaB; yoaB (1920554-1920898) (0)rev.; s. a. pabC (1282057) |
| 134.86 | 1927593 | 1927993 | 1 | yoaE (1926499-1928055): Sequenz nur 85% |
| 064.81 | 1941228 | 1941628 | 0 | prc (1941129-1943177): carboxy-terminal protease for penicillin-binding protein 3; P > proQ-prc? |
| 019.86 | 1963367 | 1963767 | 0 | mig-3 (1963471-1964352) |
| 007.13 | 1989745 | 1990145 | 1 | ruvA (1990068-1990679)-ruvB (1989049-1990059), Holliday junction helicase subunit B resp. A (branch migration, repair); essential in dam |
| 084.67 | 1995747 | 1996147 | 1 | aspS (1995106-1996878): aspartate tRNA synthetase; P > aspS |
| 019.48 | 2017315 | 2017715 | 0 | cheA (2017173-2019188): Chemotaxis and mobility; sensory transducer kinase between chemo-signal; P > motA-motB-cheA-cheW? |
| 014.67 | 2041538 | 2041938 | 0 | YecS (2041356-2042024): putative transport system permease protein; P-yedO-P?-yecS-P?-yceC-P |
| 023.95 | 2141346 | 2141746 | 1 | sopA (2141565-2143913); Secreted protein; S. dublin; polar effect on phsABC? |
| 118.44 | 2144003 | 2144403 | 1 | sbcB (2144256-2145686): exonuclease I, 3' → 5' specific; deoxyribophosphodiesterase |
| 118.53 | 2145760 | 2146160 | 0 | yeeF (2145822-2147186): putative APC family, amino acid transport protein; polarer Effekt? |
| 110.96 | 2155763 | 2156163 | 0 | hisF (2155365-2156141): imidazole glycerol phosphate synthase, subunit with HisH |
| 034.84 | 2163175 | 2163575 | 0 | rfbK (2162428-2163861): (manB), phosphomannomutase; (S. enterica); P > rfbK-ORF261-ORF431-ORF708-mtfABC |
| 118.57 | 2168012 | 2168412 | 1 | rfbV(2167614-2168615) |
| 077.18 | 2193768 | 2194168 | 1 | wcaF (2193743-2194297): putative transferase; P > wcaDEFGHIJ . . . ? |
| 079.35 | 2195255 | 2195655 | 0 | wcaD (2195072-2196286): putative |

TABLE 3-continued

| Number | insertion: start | insertion: stop | orientation | affected gene |
|---|---|---|---|---|
| | | | | glycosyl transferase in colanic acid biosynthesis |
| 053.94 | 2248264; 2248825 | 2248664; 2249225 | 0 | mrp (2248460-2249569): putative ATP-binding protein; yehE (2247901-2248182) |
| 085.03 | 2250136 | 2250536 | 0 | metG (2249653-2251767): methionine tRNA synthetase |
| 082.65 | 2286756 | 2287156 | 0 | mglB (2286613-2287611): ABC superfamily galactose transport protein; polar effect |
| 092.68 | 2322398 | 2322798 | 0 | bcr (2322477-2323667): MFS family multidrug transport protein, bicyclomycin resistance protein (2nd module); polar effect on rsuA (2323695-2324390)(1): 16S rRNA pseudouridylate 516 |
| 008.44 | 2340969 | 2341369 | 0 | H2 (2340879-2343245), SspH1; secreted protein; operon? |
| 139.78 | 2356393 | 2356793 | 1 | napA (2356412-2358898): periplasmic nitrate reductase, large subunit, in complex with NapB |
| 114.62 | 2370454 | 2370854 | 0 | rcsC (2370739-2373585)(−): sensory histidine kinase in two-component regulatory regulates colanic capsule biosynthesis; rcsB (2369986-2370636) + response regulator (positive) in two- |
| 085.90 | 2374649 | 2375049 | 0 | gyrA (2373703-2376339): DNA gyrase, subunit A, type II topoisomerase |
| 077.50 | 2377384 | 2377784 | 0 | orf2 2376749-2377951); orf1 (2377966-2379291) |
| 018.33 | 2377791 | 2378191 | 1 | orf1 |
| 133.76 | 2399418 | 2399818 | 1 | yfaX (2399425-2400207) |
| 091.45 | 2402940 | 2403340 | 0 | pmrG (2403059-2403664): polymyxin resistance protein G; yfaO (2402589-2403014) |
| 039.68 | 2488418 | 2488818 | 0 | fabB (2488614-2489828): 3-oxoacyl-[acyl-carrier-protein] synthase I; orf (2487860-2488516); survival in stationary phase; ts-mutant |
| 005.35 | 2502143 | 2502543 | 0 | fadL (2502381-2503694): transport of long-chain fatty acids; survival in stationary phase |
| 131.69 | 2539341 | 2539741 | 0 | lig (2538993-2541008): DNA-Ligase |
| 013.28 | 2598117 | 2598517 | 1 | DapE (2597686-2598813): N-succinyl-diaminopimelate deacylase |
| 003.94 | 2610290 | 2610690 | 0 | yfgE (2609852-2610577), uraA (2610648-2611937) |
| 042.53 | 2647762 | 2648162 | 0 | sinI (2647584-2648543) |
| 016.85 | 2652282; 2652505; 2652553 | 2652682; 2652905; 2652953 | 1; 0; 0 | engA (2651449-2652921): putative GTP-binding factor; EngA s. paper |
| 080.08 | 2655093 | 2655493 | 1 | hisS (2654863-2656137): histidin-tRNA synthetase; P? |
| 133.20 | 2763882 | 2764282 | 0 | orf (2763703-2764314) |
| 001.25 | 2787446 | 2787846 | 1 | yfif (2787405-2788442); hypoth. TRNA/rRNA methyltransferase |
| 119.40 | 2793563 | 2793963 | 1 | pssA (2792647-2794001): phosphatidylserine synthase (CDP-diacylglycerol-serine O-phosphatidyltransferase) (2nd module); E. coli must be supplemented with |
| 078.78 | 2796631 | 2797031 | 1 | rrfG (2796433-2796554): 5SrRNA |
| 059.60 | 2797043; viele weitere | 2797443 | 1; 1; 0; 1; 1 | rrlG (2796748-2799757) |
| 065.88 | 2801158 | 2801558 | 1 | rrsG (2800114-2801653); 16S rRNA |
| 072.88 | 2815439 | 2815839 | 0 | TrmD (2815250-2816017): aminoacyl tRNA synthetase; tRNA methyltransferase; P > rpoP-rimM-?-trmD-rplS |
| 038.82 | 2821376; 2821390 | 2821776; 2821790 | 1; 0 | orf (2820936-2821541); grpE (2821576-2822160): phage lambda replication; host DNA synthesis; heat shock protein; protein repair; P > grpE |
| 093.21 | 2972914 | 2973314 | 1 | alaS (2971360-2973990): alanyl-tRNA synthetase |
| 026.67 | 3025863 | 3026263 | 1 | sipA (3024668-3026725); P > sipC-sipD-sipA-sipF? |
| 029.64 | 3050104 | 3050504 | 1 | mutS (3050268-3052835): mismatch repair, orf (3049588-3050109) (1), or cysD/cysN |
| 054.71 | 3056391 | 3056791 | 0 | orf (3055538-3057034) |

TABLE 3-continued

| Number | insertion: start | insertion: stop | orientation | affected gene |
|---|---|---|---|---|
| 073.50 | 3098077 | 3098477 | 0 | eno (3097353-3098651), enolase, enzyme; Energy metabolism, carbon: Glycolysis, P > ygcG-eno-pyrG < P (*E. coli*); essential (ts) |
| 057.87 | 3098451; 3099550; 3099954; 3099237 | 3098851; 3099950; 3100354; 3099637 | 1; 0; 1; 0 | PyrG (3098734-3100371): Nucleotide interconversions; CTP synthetase; P > pyrG-eno; polar effect on eno(essential) |
| 014.65 | 3138341 | 3138741 | 0 | orf (3137893-3138780) |
| 137.07 | 3154480 | 3154880 | 1 | recC (3152701-3156072): exonuclease V, subunit |
| 131.26 | 3171641 | 3172041 | 1 | orf (3171562-3172674) |

TABLE 4

| number | fragment start | fragment stop | orientation |
|---|---|---|---|
| 048.07 | 0019501 | 0019901 | 1 |
| 001.63 | 0069970 | 0070370 | 0 |
| 019.09 | 0107431 | 0107831 | 1 |
| 005.53 | 0180996 | 0181396 | 1 |
| 022.64 | 0198916 | 0199316 | 0 |
| 087.21 | 0263270 | 0263670 | 0 |
| 045.43 | 0298049 | 0298449 | 1 |
| 040.95 | 0308111 | 0308511 | 1 |
| 017.53 | 0337263 | 0337463 | 0 |
| 142.79 | 0337351 | 0337751 | 1 |
| 141.87 | 0344954 | 0345354 | 1 |
| 015.89 | 0387213 | 0387613 | 1 |
| 114.48 | 0389348 | 0389748 | 0 |
| 126.37 | 0389385 | 0389785 | 0 |
| 044.95 | 0433005 | 0433405 | 1 |
| 053.54 | 0451218 | 0451618 | 0 |
| 120.47 | 0493014 | 0493414 | 1 |
| 114.44 | 0494170 | 0494570 | 1 |
| 041.38 | 0504459 | 0504859 | 0 |
| 098.87 | 0529331 | 0529731 | 1 |
| 092.44 | 0597932 | 0598332 | 1 |
| 127.23 | 0602850 | 0603250 | 0 |
| 006.91 | 0616098 | 0616498 | 0 |
| 138.14 | 0662114 | 0662514 | 1 |
| 065.56 | 0667126 | 667526 | 1 |
| 130.42 | 0678014 | 0678414 | 0 |
| 144.58 | 0789956 | 0790356 | 1 |
| 141.92 | 0829294 | 0829694 | 1 |
| 020.90 | 0854459 | 0854859 | 0 |
| 020.43 | 0878747 | 0879147 | 0 |
| 049.22 | 0921086 | 0921486 | 1 |
| 016.91 | 0929106 | 0929506 | 1 |
| 009.65 | 0931253 | 0931653 | 1 |
| 064.06 | 0952628 | 0953028 | 1 |
| 136.34 | 0955409 | 0955809 | 1 |
| 025.70 | 1007534 | 1007934 | 0 |
| 088.15 | 1063508 | 1063908 | 0 |
| 125.92 | 1095712 | 1096112 | 0 |
| 007.22 | 1879280 | 1879680 | 1 |
| 077.32 | 1917904 | 1918304 | 0 |
| 008.66 | 1920897 | 1921297 | 0 |
| 134.86 | 1927593 | 1927993 | 1 |
| 064.81 | 1941228 | 1941628 | 0 |
| 055.61 | 1950548 | 1950948 | 0 |
| 064.86 | 1950566 | 1950966 | 1 |
| 019.86 | 1963367 | 1963767 | 0 |
| 019.48 | 2017315 | 2017715 | 0 |
| 014.67 | 2041538 | 2041938 | 0 |
| 023.95 | 2141346 | 2141746 | 1 |
| 118.44 | 2144003 | 2144403 | 1 |
| 118.53 | 2145760 | 2146160 | 0 |
| 110.96 | 2155763 | 2156163 | 0 |
| 034.84 | 2163175 | 2163575 | 0 |
| 118.57 | 2168012 | 2168412 | 1 |
| 077.18 | 2193768 | 2194168 | 1 |
| 079.35 | 2195255 | 2195655 | 0 |
| 032.78 | 2236668 | 2237068 | 1 |
| 053.94 | 2248264 | 2248664 | 0 |
| 092.68 | 2322398 | 2322798 | 0 |
| 139.78 | 2356393 | 2356793 | 1 |
| 114.62 | 2370454 | 2370854 | 0 |
| 077.50 | 2377384 | 2377784 | 0 |
| 018.33 | 2377791 | 2378191 | 1 |
| 133.76 | 2399418 | 2399818 | 1 |
| 039.68 | 2488418 | 2488818 | 0 |
| 005.35 | 2502143 | 2502543 | 0 |
| 076.64 | 2522598 | 2522198 | 1 |
| 040.36 | 2548092 | 2548492 | 1 |
| 003.94 | 2610290 | 2610690 | 0 |
| 133.20 | 2763882 | 2764282 | 0 |
| 027.15 | 2773624 | 2774024 | 0 |
| 001.25 | 2787446 | 2787846 | 1 |
| 053.61 | 2968054 | 2968454 | 0 |
| 065.04 | 3010259 | 3010661 | 1 |
| 026.67 | 3025863 | 3026263 | 1 |
| 067.48 | 3030094 | 3030494 | 1 |
| 054.71 | 3056391 | 3056791 | 0 |
| 131.26 | 3171641 | 3172041 | 1 |
| 027.15 | 1101114 | 1101514 | 1 |
| 074.30 | 1113807 | 1114207 | 0 |
| 049.09 | 1138706 | 1139106 | 0 |
| 026.65 | 1184282 | 1184682 | 1 |
| 087.94 | 1205128 | 1205528 | 1 |
| 007.19 | 1217392 | 1217792 | 1 |
| 083.80 | 1218315 | 1218715 | 1 |
| 057.54 | 1222717 | 1223117 | 0 |
| 064.21 | 1231333 | 1231733 | 1 |
| 112.65 | 1245246 | 1245646 | 0 |
| 062.37 | 1274223 | 1274623 | 0 |
| 088.92 | 1324663 | 1325063 | 1 |
| 045.18 | 1331865 | 1332265 | 1 |
| 068.91 | 1337846 | 1338246 | 1 |
| 129.25 | 1436521 | 1436921 | 0 |
| 061.66 | 1441503 | 1441903 | 1 |
| 030.54 | 1472976 | 1473376 | 1 |
| 014.38 | 1512482 | 1512882 | 0 |
| 028.89 | 1530500 | 1530900 | 1 |
| 089.62 | 1550161 | 1550561 | 0 |
| 066.28 | 1591866 | 1592266 | 0 |
| 009.83 | 1601741 | 1602141 | 0 |
| 098.42 | 1618929 | 1619329 | 0 |
| 119.17 | 1627904 | 1628304 | 1 |
| 009.47 | 1633672 | 1634072 | 0 |
| 125.26 | 1639682 | 1640082 | 1 |
| 144.05 | 1642004 | 1642404 | 1 |
| 024.31 | 1658266 | 1658666 | 1 |
| 089.17 | 1664180 | 1664580 | 1 |
| 042.26 | 1727005 | 1727405 | 0 |
| 131.63 | 1741057 | 1741457 | 1 |
| 028.68 | 1757740 | 1758140 | 0 |

TABLE 4-continued

| number | fragment start | fragment stop | orientation |
|---|---|---|---|
| 013.17 | 1796398 | 1796798 | 1 |
| 068.19 | 1801641 | 1802041 | 0 |
| 079.16 | 1843617 | 1844017 | 1 |
| 044.34 | 1850066 | 1850466 | 1 |
| 089.17 | 1858271 | 1858671 | 0 |
| 007.22 | 1879280 | 1879680 | 1 |
| 039.33 | 3125329 | 3125729 | 0 |
| 014.65 | 3138341 | 3138741 | 0 |
| 137.07 | 3154480 | 3154880 | 1 |
| 033.16 | 3186873 | 3187273 | 0 |
| 107.77 | 3246136 | 3246536 | 0 |
| 037.49 | 3249369 | 3249769 | 0 |
| 142.56 | 3252003 | 3252403 | 0 |
| 040.48 | 3310886 | 3311286 | 0 |
| 087.44 | 3447439 | 3447839 | 0 |
| 062.51 | 3448153 | 3448553 | o |
| 069.22 | 3508826 | 3509226 | 0 |
| 048.42 | 3908804 | 3909204 | 1 |
| 129.28 | 3908870 | 3909270 | 1 |
| 130.60 | 3915002 | 3915402 | 0 |
| 063.31 | 4046410 | 4046810 | 0 |
| 062.24 | 4063750 | 4064150 | 0 |
| 027.13 | 4106905 | 4107305 | 0 |
| 132.58 | 4120506 | 4120906 | 0 |
| 002.74 | 41241626 | 4125026 | 1 |
| 063.51 | 4183/40 | 4184140 | 1 |
| 038.30 | 4184136 | 4184536 | 0 |
| 131.34 | 4216712 | 4217112 | 0 |
|  | 4319806 | 4320206 | 1 |
| 073.34 | 4384326 | 4384726 | 1 |
| 053.29 | 4386101 | 4386501 | 0 |
| 010.49 | 4479697 | 4480097 | 1 |
| 126.89 | 4497591 | 4497991 | 1 |
| 041.27 | 4500041 | 4500441 | 1 |
| 057.88 | 4506243 | 4506643 | 1 |
| 059.26 | 4517808 | 4518208 | 0 |
| 061.57 | 4549863 | 4550263 | 0 |
| 121.51 | 4586654 | 4587054 | 0 |
| 010.36 | 4606191 | 4606591 | 1 |
| 067.80 | 4611503 | 4611903 | 0 |
| 066.67 | 4636387 | 4636787 | 0 |
| 026.79 | 4651369 | 4651769 | 1 |
| 067.29 | 4670607 | 4671007 | 1 |
| 116.68 | 4714018 | 4714418 | 1 |
| 090.30 | 4715929 | 4716329 | 1 |
| 067.78 | 4856084 | 4856484 | 0 |

LITERATURE

Akerley, B. J., E. J. Rubin, A. Camilli, D. J. Lampe, H. M. Robertson, and J. J. Mekalanos. 1998. Systematic identification of essential genes by in vitro mariner mutagenesis. Proc Nalt Acad Sci USA 95:8927-32.

Arigoni, F., F. Talabot, M. Peitsch, M. D. Edgerton, E. Meldrum, E. Allet, R. Fish, T. Jamotte, M. L. Curchod, and H. Loferer. 1998. A genome-based approach for the identification of essential bacterial genes. Nat Biotechnol. 16:851-6.

Biawas, I., A. Gruss, S. D. Ehrlich, and E. Maguln. 1993. High-efficiency gene inactivation and replacement system for gram-positive bacteria. J Bacteriol. 175:3628-35.

Brown, E. D., E. I. Vivas, C. T. Walsh, and R. Kolter. 11995. MurA (MurZ), the enzyme that catalyzes the first committed step in peptidoglycan biosynthesis, is essential in Escherichia coli. J Bacteriol. 177:4194-7.

Chalker A F, Minehart N W, Hughes N J, Koretke K K, Lonetto M A, Brinkman K K, Warren P V, Lupas A, Stanhope M J, Brown J R. and H. P S. 2001. Systematic Identification of Selective Essential Genes in Helicobacter pylori by Genome Prioritization and Allelic Replacement Mutagenesis. J Bacteriol. 183:1259-1268.

Cooney, M, G. Czemuszewicz, E. H. Postel, S. J. Flint, and M. E. Hogan. 1988. Site-specific oligonucleotide binding represses transcription of the human c-myc gene in vitro. Science. 241:458-9.

Froussard, P. 1992. A random-PCR method (rPCR) to construct whole cDNA library from low amounts of RNA. Nucleic Acids Res. 20:2900.

Fuchs et al. 2001. Unpublished results.

Hare, R. S., S. S. Walker, T. E. Dorman, J. R. Greene, L. M. Guzman, T. J. Kenney, M. C. Sulavik, K. Baradaran, C. Houseweart, H. Yu, Z. Foldes, A. Motzer, M. Walbridge, G. H. Shimer, Jr., and K. J. Shaw. 2001. Genetic footprinting in bacteria. J Bacteriol. 183:1694-706.

Harris, S. D., J. Cheng, T. A. Pugh, and J. R. Pringle. 1992. Molecular analysis of Saccharomyces cerevisiae chromosome 1. On the number of genes and, the identification of essential genes using temperature-sensitive-lethal mutations. J Mol Biol. 225:53-65.

Hashimoto-Gotoh, T., F. C. Franklin, A. Nordheim, and K. N. Timmis. 1981. Specific-purpose plasmid cloning vectors. I. Low copy number, temperature-sensitive, mobilization-defective pSC101-derived containment vectors. Gene. 16:227-35.

Hensel, M., J. E. Shea, C. Gleeson, M. D. Jones, E. Dalton, and D. W. Holden. 1995. Simultaneous identification of bacterial virulence genes by negative selection. Science. 269,400-3.

Holden, D. W., and M. Hensel. 1998. Signature tagged mutagenesis. Methods in Microbiology 27: 359-369.

Hutchison, C. A., S. N. Peterson, S. R. Gill, R. T. Cline, O. White, C. M. Fraser, H. O. Smith, and J. C. Venter. 1999. Global transposon mutagenesis and a minimal Mycoplasma genome. Science. 286:2165-9.

Judson, N., and J. J. Mekalanos. 2000. Transposon-based approaches to identify essential bacterial genes. Trends Microbiol. 8:521-6.

Judson, N., and J. J. Mekalanos. 2000. TAreaOut, a transposon-based approach to identify and characterize essential bacterial genes. Nat Biotechnol. 18:740-5.

Kohler, G., and C. Milstein. 1975. Continuous cultures of fused cells secreting antibody of predefined specificity. Nature. 256:495-7.

Kok, J., J. M. van der Vossen, and G. Venema. 1984. Construction of plasmid cloning vectors for lactic streptococci which also replicate in Bacillus subtilis and Escherichia coli. Appl Environ Microbiol. 48:726-31.

Lehoux, D. E., F. Sanschagrin, and R. C. Levesque. 1999. Defined oligonucleotide tag pools and PCR screening in signature-tagged mutagenesis of essential genes from bacteria. Biotechniques. 26:473-8, 480.

Link, A. J., D. Phillips, and G. M. Church. 1997. Methods for generating precise deletions and insertions in the genome of wild-type Escherichia coli: application to open reading frame characterization. J Bacteriol. 179:6228-37.

Loferer, I., I., Jacobi, I. Posch, I. Gauss, I. Meier-Ewert, and I. Seizinger. 2000. Integrated bacterial genomics for the discovery of novel antimicrobials. Drug Discov Today. 5:107-114.

Maguin, E., P. Duwat, T. Hege, D. Ehrlich, and A. Gruss. 1992. New thermosensitive plasmid for gram-positive bacteria. J Bacteriol. 174:5633-8.

Martin, P. K., T. Li, D. Sun, D. P. Blek, and M. B. Schmid. 1999. Role in cell permeability of an essential two-component system in Staphylococcus aureus. J. Bacteriol. 181; 3666-73.

Metcalf, W. W., W. Jiang, and B. L. Wanner, 1994. Use of the rep technique for allele replacement to construct new *Escherichia coli* hosts for maintenance of R6K gamma origin plasmids at different copy numbers. Gene. 138:1-7.

Metcalf, W. W., W. Jiang, L. L. Daniels, S. K. Kim, A. Haldimann, and B. L. Wanner. 1996. Conditionally replicative and conjugative plasmids carrying lacZ alpha for cloning, mutagenesis, and allele replacement in bacteria. Plasmid. 35:1-13

Mushegian, A. R., and E. V. Koonin. 1996. A minimal gene set for cellular life derived by comparison of complete bacterial genomes [see comments]. Proc Nan Acad Sci USA. 93:10288-73.

Okano, H., J. Aruga, T. Nakagawa, C. Shiota, and K Mikoshiba. 1991. Myelin basic protein gene and the function of antisense RNA in its repression in myelin-deficient mutant mouse. J Neurochem. 56:560-7.

Rubin, E. J., B. J. Akerley, V. N. Novik, D. J. Lampe, R. N. Husson, and J. J. Mekalanos. 1999. In vivo transposition of mariner-based elements in enteric bacteria and mycobacteria. Proc Nab Acad Sci USA 96 1645-50.

Reich, K. A, L. Chovan, and P. Hessler. 1999. Genome scanning in Haemophilus influenzae for identification of essential genes. J Bacteriol. 181:4961-8.

Sambrook, J., E. F. Fritsch, and T. Maniatis. 1989. Molecular cloning: a laboratory manual, 2nd ed. Cold Spring Harbor Laboratory, Cold Spring Harbor, N.Y.

Schmid, M. B., N. Kapur, D. R. Isaacson, P. Lindroos, and C. Sharpe. 1989. Genetic analysis of temperature-sensitive lethal mutants of *Salmonella typhimurium*. Genetics. 123: 625-33.

Schmid, M. B. 1998. Novel approaches to the discovery of antimicrobial agents. Curr Opin Chem Biol. 2:529-34.

Taklff, M. E., T. Baker, T. Copeland, S. M. Chen, and D. L Court 1992. Locating essential *Escherichia coli* genes by using mini-Tn10 transposons: the pdxJ operon. J Bacteriol 174:1544-53.

Winzeler, E. A., D. D. Shoemaker, A. Astromoff, H. Liang, K. Anderson, B. Andre, R. Bangham, R. Benito, J. D. Boeke, H. Bussey, A. M. Chu, C. Connelly, K. Davis, F. Dietrich, S. W. Dow, M. E I Bakkoury, F. Foury, S. H. Frtend, E. Gentalen, G. Giaever, J. H. Hegemann, T. Jones, M. Laub, H. Liao, R. W. Davis, and at al. 1999. Functional characterization of the *S. cerevisiae* genome by gene deletion and parallel analysis. Science. 285:901-6.

Wong, S. M., and J. J. Mekalanos. 2000. Genetic footprinting with manner-based transposition in *Pseudomonas aeruginosa*. Proc Natl Acad Sci USA 97:10191-6.

The invention claimed is:

1. Method for the identification of obligatory essential microbial nucleic acid sequences comprising the steps
    (a) providing a conditionally replicating vector, comprising
        (i) a conditionally replicating origin of replication which can be activated or inactivated by changing the conditions under which a host cell is cultivated
        (ii) a selectable marker
        (iii) nucleic acid sequences of a microorganism
    (b) transforming microbial host cells with said conditionally replicating vector, wherein the host cells is selected such that the nucleic acid sequence of (a) (iii) is homologous to an endogenous nucleic acid sequence of the host cell in order to allow homologous recombination,
    (c) subjecting the transformed host cells to insertional duplication mutagenesis by homologous recombination, resulting in viable and non viable (lethal) integrants,
    (d) directly identifying lethal integrants by separating viable and nonviable integrants of step (c) under permissive conditions versus non-permissive conditions for replication of the conditionally replicating vector of (a),
    (e) characterizing nucleic acid sequence from lethal integrants and/or polypeptides encoded thereby which are obligatory essential for the viability of said microorganism.

2. Method of claim 1, wherein step (c) comprises a substantially genome saturating mutagenesis.

3. Method of claim 1, wherein said nucleic acid sequence of step (a) is derived from a microorganism selected from bacteria and yeast.

4. Method of claim 1, wherein insertional duplication mutagenesis of step (c) takes place under permissive conditions, allowing the replication of the vector provided in step (a).

5. Method of claim 1, wherein identifying lethal integrants of step (d) is performed by replica plating.

6. Method of claim 1, wherein characterizing the lethal integrants in step (d) comprises a nucleic acid amplification.

7. The method of claim 1, wherein said nucleic acid sequences and/or polypeptides encoded thereby which are obligatory essential for the viability of said microorganism are characterized in step (e) by comparing the genomes of said lethal integrants.

8. The method of claim 7, comprising identifying orthologs in the genomes of said lethal integrants.

9. The method for the identification of nucleic acid sequences according to claim 1, wherein said insertional duplication mutagenesis is a genome-saturating mutagenesis.

10. The method according to claim 3, wherein said bacteria is a Gram positive or Gram negative bacteria.

11. The method according to claim 6, wherein said nucleic acid amplification is polymerase chain reaction.

12. A method for the identification and/or priorization of drug targets in microorganisms, comprising
    (a) providing a conditionally replicating vector, comprising
        (i) a conditionally replicating origin of replication which can be activated or inactivated by changing the conditions under which a host cell is cultivated,
        (ii) a selectable marker,
        (iii) nucleic acid sequences of a microorganism,
    (b) transforming microbial host cells with said conditionally replicating vector, wherein the host cells is selected such that the nucleic acid sequence of (a) (iii) is homologous to an endogenous nucleic acid sequence of the host cell in order to allow homologous recombination,
    (c) subjecting the transformed host cells to insertional duplication mutagenesis by homologous recombination, resulting in viable and non viable (lethal) integrants,
    (d) directly identifying lethal integrants by separating viable and nonviable integrants of step (c) under permissive conditions versus non-permissive conditions for replication of the conditionally replicating vector of (a),
    (e) characterizing nucleic acid sequences, from lethal integrants and/or polypeptides encoded thereby, which are obligatory essential for the viability of said microorganism as potential drug targets.

* * * * *